United States Patent
Kanayama et al.

(10) Patent No.: US 10,959,704 B2
(45) Date of Patent: Mar. 30, 2021

(54) ULTRASONIC DIAGNOSTIC APPARATUS, MEDICAL IMAGE PROCESSING APPARATUS, AND MEDICAL IMAGE PROCESSING METHOD

(71) Applicant: Toshiba Medical Systems Corporation, Otawara (JP)

(72) Inventors: Yuko Kanayama, Nasushiobara (JP); Tetsuya Kawagishi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 1213 days.

(21) Appl. No.: 14/244,969

(22) Filed: Apr. 4, 2014

(65) Prior Publication Data

US 2015/0080730 A1    Mar. 19, 2015

Related U.S. Application Data

(63) Continuation of application No. PCT/JP2013/075207, filed on Sep. 18, 2013.

(51) Int. Cl.
*A61B 8/08* (2006.01)
*G06T 7/00* (2017.01)
(Continued)

(52) U.S. Cl.
CPC ............ *A61B 8/5207* (2013.01); *A61B 8/485* (2013.01); *G01S 7/52022* (2013.01);
(Continued)

(58) Field of Classification Search
CPC ......... A61B 8/485; A61B 8/14; A61B 8/5207; A61B 8/0858; A61B 8/469; A61B 8/5223;
(Continued)

(56) References Cited

U.S. PATENT DOCUMENTS

| 8,961,418 B2* | 2/2015 | Fan | A61B 8/485 |
|---|---|---|---|
| | | | 600/438 |
| 9,468,421 B2* | 10/2016 | Benson | A61B 8/463 |

(Continued)

FOREIGN PATENT DOCUMENTS

| CN | 102667522 A | 9/2012 | |
|---|---|---|---|
| CN | 102293669 | * 12/2013 | ........... A61B 8/0883 |

(Continued)

OTHER PUBLICATIONS

Combined Office Action and Search Report dated Feb. 3, 2016 in Chinese Patent Application No. 201380001735.X (with English translation of category of cited documents).

(Continued)

*Primary Examiner* — Amanda Lauritzen Moher
(74) *Attorney, Agent, or Firm* — Oblon, McClelland, Maier & Neustadt, L.L.P.

(57) ABSTRACT

According to one embodiment, an ultrasonic diagnostic apparatus includes an ultrasonic probe, transmission unit transmitting a first ultrasonic wave for generating a shear wave in an object to a first region and a second ultrasonic wave to a second region, reception unit generating a reception signal based on the second ultrasonic wave, displacement amount calculation unit calculating a displacement amount of a tissue accompanying propagation of the shear wave to the second region by using the reception signal, arrival time decision unit deciding an arrival time when the shear wave has arrived at each position in the second region, based on a temporal change in the displacement amount concerning the each position, and image generation unit generating based on the arrival time and predetermined pixel values corresponding to the arrival times, a shear wave arrival time image with the pixel values being assigned corresponding to the arrival times.

12 Claims, 11 Drawing Sheets

(51) Int. Cl.
*G01S 15/89* (2006.01)
*G01S 7/52* (2006.01)
*A61B 8/00* (2006.01)

(52) U.S. Cl.
CPC ...... *G01S 7/52042* (2013.01); *G01S 7/52071* (2013.01); *G01S 7/52095* (2013.01); *G01S 15/8915* (2013.01); *G01S 15/8979* (2013.01); *G06T 7/0012* (2013.01); *A61B 8/469* (2013.01)

(58) Field of Classification Search
CPC ............. G01S 15/8915; G01S 15/8979; G01S 7/52022; G01S 7/52036; G01S 7/52042; G01S 7/52071; G01S 7/52095; G03B 42/06; G06T 7/0012
See application file for complete search history.

(56) References Cited

U.S. PATENT DOCUMENTS

| | | | | |
|---|---|---|---|---|
| 9,554,770 | B2* | 1/2017 | Fan | A61B 8/08 |
| 2002/0010398 | A1 | 1/2002 | Bonnefous et al. | |
| 2007/0167777 | A1* | 7/2007 | Abe | A61B 8/488 |
| | | | | 600/441 |
| 2010/0016718 | A1 | 1/2010 | Fan et al. | |
| 2010/0286516 | A1* | 11/2010 | Fan | A61B 8/08 |
| | | | | 600/438 |
| 2012/0089019 | A1* | 4/2012 | Fan | A61B 8/485 |
| | | | | 600/437 |
| 2012/0123263 | A1 | 5/2012 | Osaka et al. | |
| 2013/0066204 | A1* | 3/2013 | Fan | A61B 8/0858 |
| | | | | 600/438 |
| 2013/0131511 | A1 | 5/2013 | Peterson et al. | |
| 2013/0218011 | A1* | 8/2013 | Benson | A61B 8/485 |
| | | | | 600/438 |
| 2015/0164480 | A1* | 6/2015 | Watanabe | A61B 8/463 |
| | | | | 600/438 |

FOREIGN PATENT DOCUMENTS

| | | | | |
|---|---|---|---|---|
| CN | 104605890 | * | 5/2015 | ............ A61B 8/08 |
| CN | 105232085 | * | 1/2016 | ............ A61B 8/00 |
| JP | 2003-530941 A | | 10/2003 | |
| JP | 2012-81269 A | | 4/2012 | |
| JP | 2013-512026 A | | 4/2013 | |
| WO | WO 2011-001776 A1 | | 1/2011 | |
| WO | WO 2011-004661 A1 | | 1/2011 | |

OTHER PUBLICATIONS

International Search Report dated Oct. 15, 2013 in PCT/JP2013/075207(submitting English translation only, previously filed).

* cited by examiner

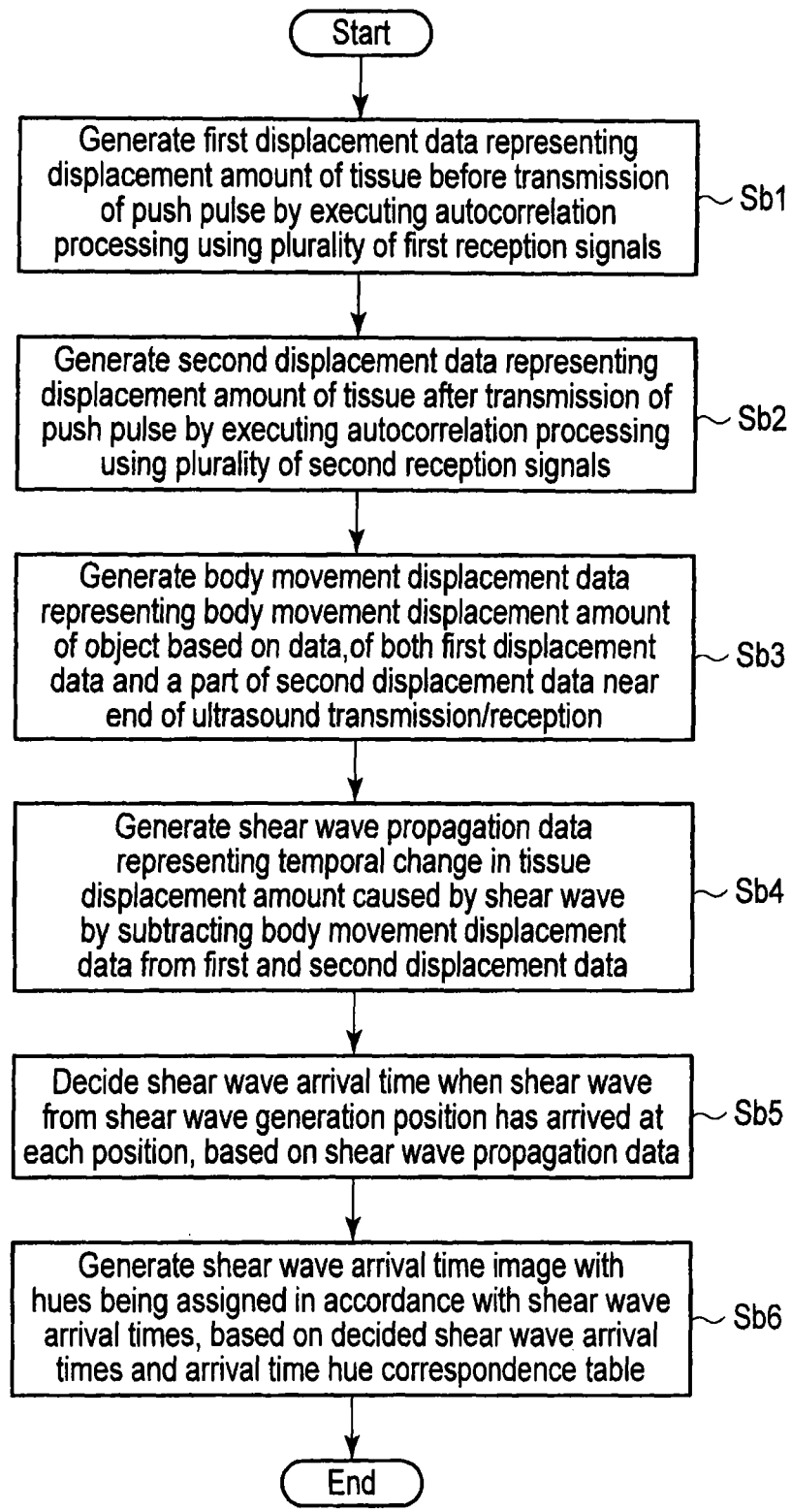
F I G. 4

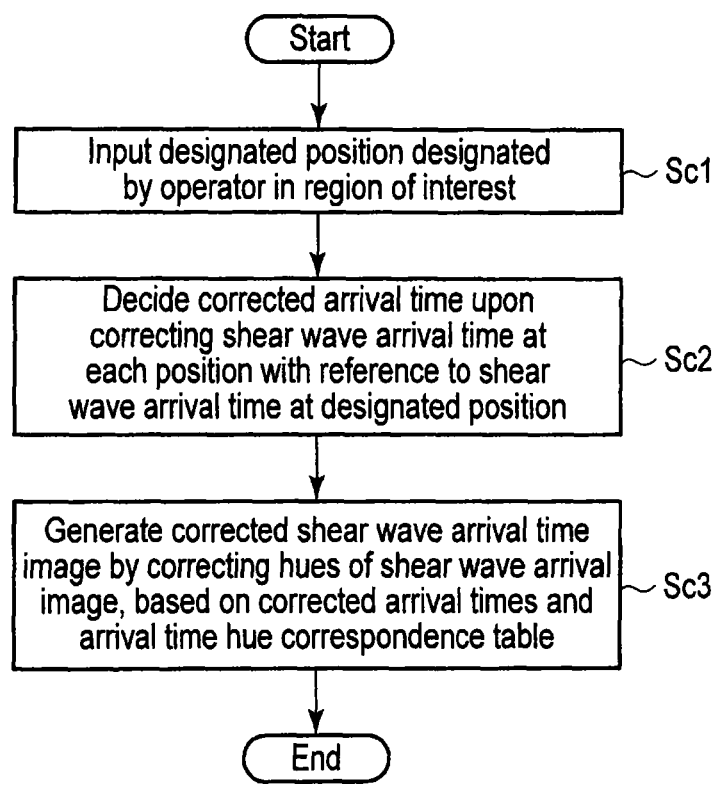
F I G. 10

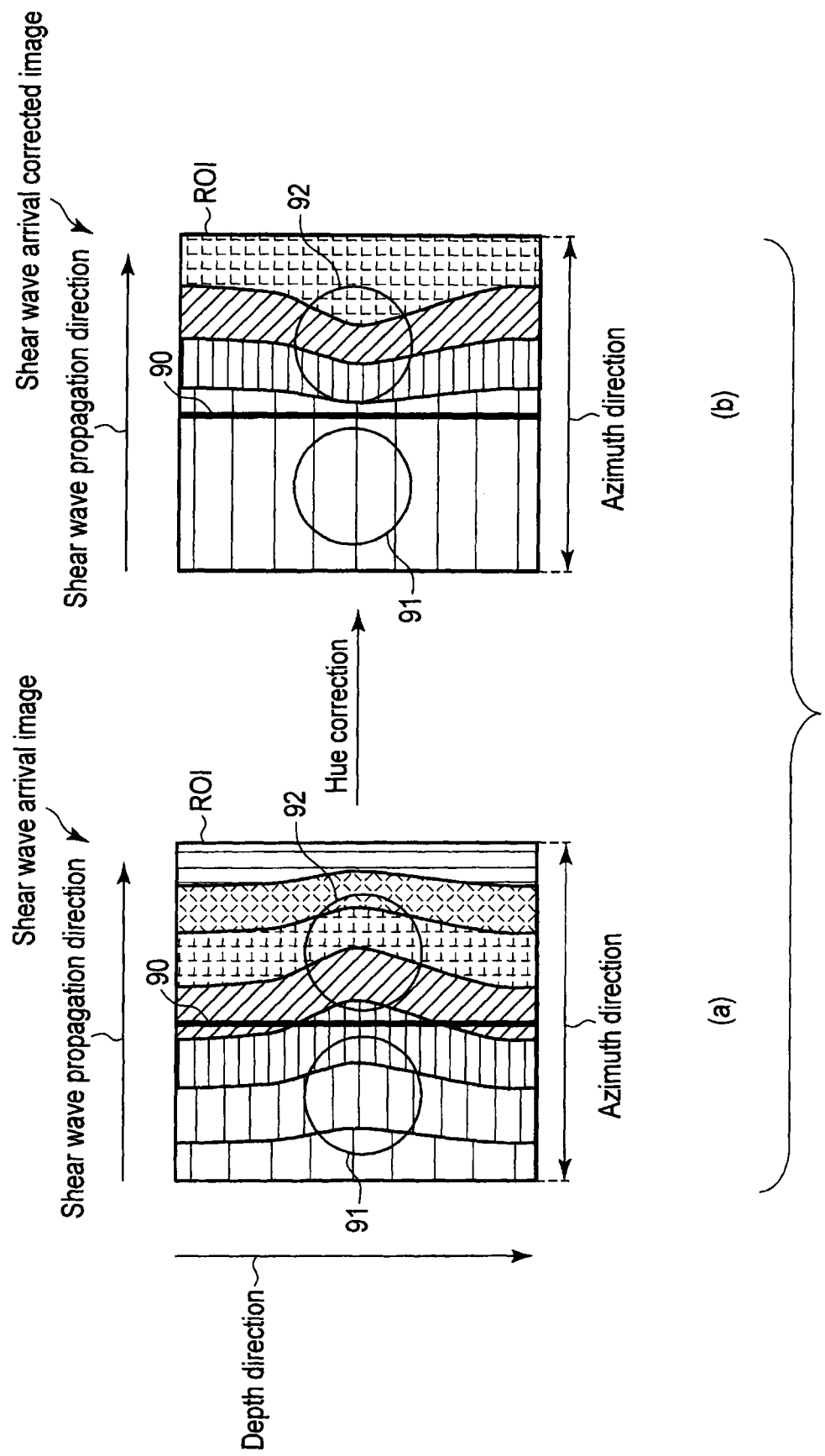
F I G. 11

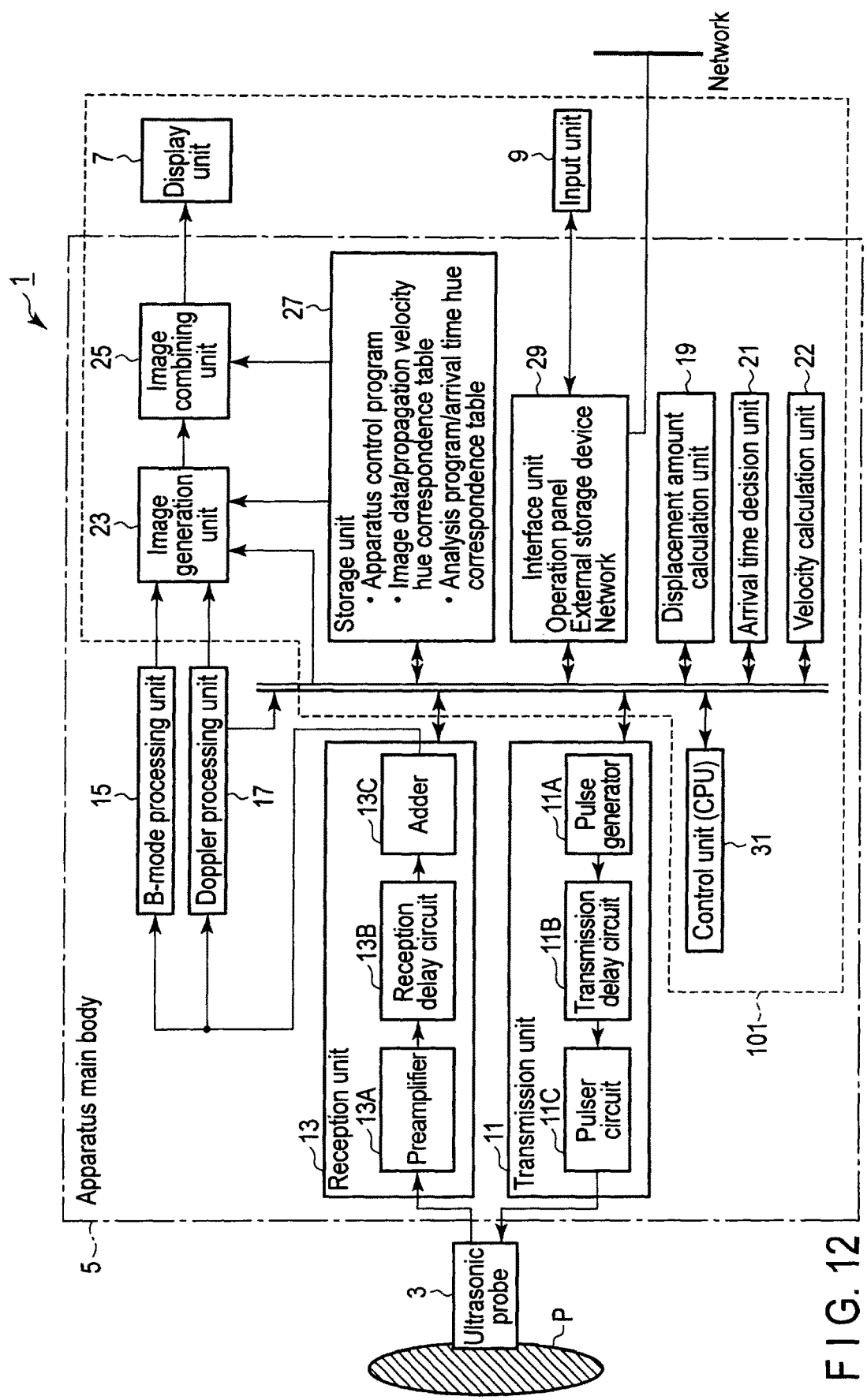
F I G. 12

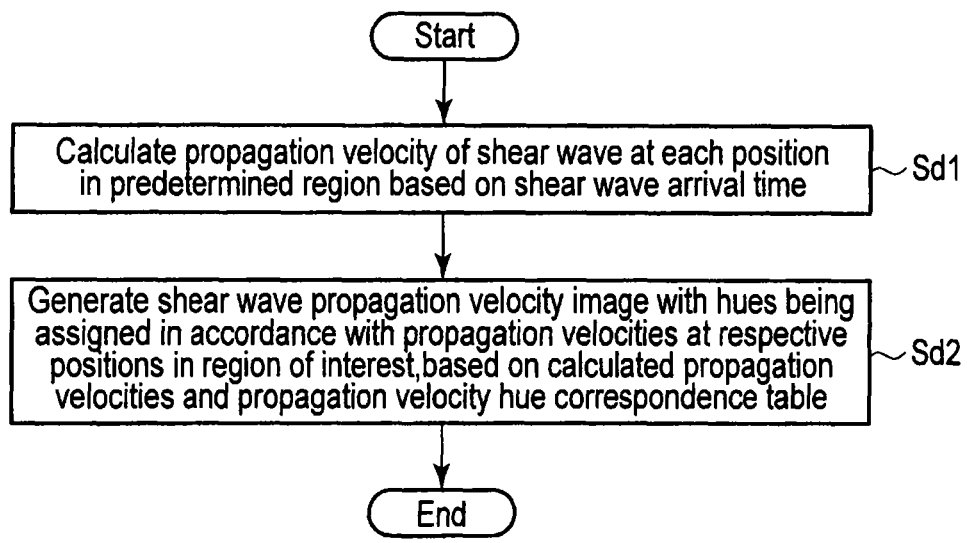
F I G. 13
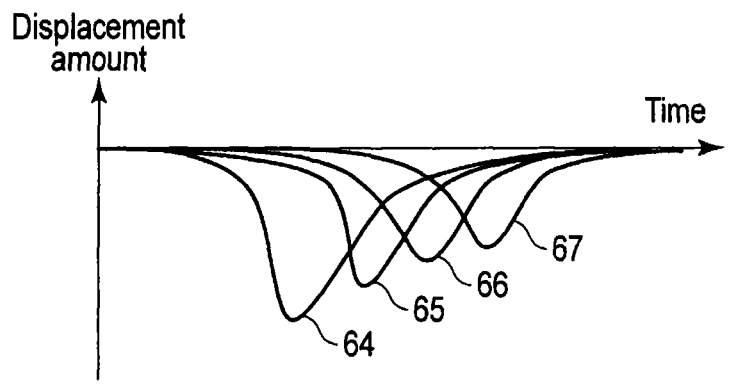
F I G. 14
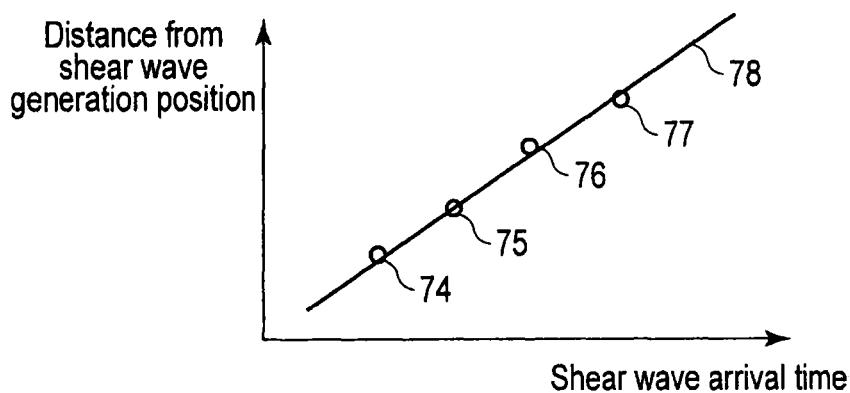
F I G. 15

ULTRASONIC DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is a Continuation application of PCT Application No. PCT/JP2013/075207, filed Sep. 18, 2013 which is incorporated herein by reference.

FIELD

Embodiments described herein relate generally to an ultrasonic diagnostic apparatus, medical image processing apparatus, and medical image processing method which image organs in an object by scanning in the object and diagnose a disease and the like in the object.

BACKGROUND

An ultrasonic diagnostic apparatus can display in real time how the heart beats or the fetus moves, by simply bringing an ultrasonic probe into contact with the body surface. In addition, the ultrasonic diagnostic apparatus is highly safe, and hence is repeatedly used for examination. Furthermore, the ultrasonic diagnostic apparatus is smaller in size than other medical image diagnostic apparatuses such as X-ray diagnostic apparatuses, X-ray computed tomography (to be referred to as CT hereinafter) apparatuses, and magnetic resonance imaging (to be referred to as MRI hereinafter) apparatuses. The ultrasonic diagnostic apparatus therefore has convenience of being able to be easily used for examination by being moved to the bedside. In addition, the ultrasonic diagnostic apparatus is free from the influence of radiation exposure on an object unlike medical image diagnostic apparatuses using X-rays, and hence can be used in obstetric treatment, treatment at home, and the like.

Recently, an ultrasonic diagnostic apparatus having a function of evaluating the hardness of a tissue in an object has been widely used. Hardness evaluation methods are broadly classified into two types. The first type is the method of visualizing the relative hardness of a tissue in an object from the magnitude of distortion at each point within a slice which is observed when an ultrasonic probe is pressed/released against/from a tissue in the object from its body surface. The second type is the method of observing the displacement of a tissue at each point within a slice with the lapse of time upon applying acoustic radiant power or mechanical vibration to the tissue from the body surface. More specifically, this method obtains the elastic modulus of a diagnosis target tissue by obtaining the propagation velocity of shear waves generated by acoustic radiant power or mechanical vibration.

According to the feature of the first methods, the magnitude of distortion in a local region depends on the magnitude of the movement of an ultrasonic probe by the operator. In addition, the first method evaluates the hardness of a region to which the operator pays attention (to be referred to as a target region hereinafter) in comparison with the hardness of a region (to be referred to as a peripheral region hereinafter) around the target region. That is, in the first method, the hardness of a target region is relative hardness compared with the hardness of a peripheral region.

The second method can obtain the absolute elastic modulus of a target region. More specifically, the second method acquires the displacement of a tissue in a time-series manner at each position in an object based on the passage of a generated shear wave. Note that since the displacement of a tissue includes the overall displacement of the tissue due to the body movement of an object in addition to the displacement of the tissue due to a shear wave, it is general practice to execute the processing of canceling the overall displacement of the tissue. This method then estimates the time when the displacement at each position becomes maximum as the arrival time when a shear wave has arrived at the position. The method obtains the propagation velocity of a shear wave propagating in an object based on the estimated arrival time and the distance from the position of generation of the shear wave to each position.

If, however, the direction and velocity of the overall movement of a tissue are irregular values which change in short times, it is sometime impossible to accurately cancel the overall displacement of the tissue. The displacement of a tissue due to a shear wave is minute depending on the location of a target region and the hardness of the tissue. This may make it impossible to accurately estimate an arrival time. In addition, if a shear wave is reflected/refracted at the interface between tissues and a target region includes a blood vessel to which no shear wave propagates, an arrival time may be erroneously obtained.

Assume that the overall displacement of a tissue has not accurately canceled, or a shear wave is reflected/refracted, or a target region includes a region to which no shear wave propagates. In such a case, the arrival time of a shear wave from the position of the generation of the shear wave to each position in the target region is a time point falling outside the overall range of the arrival time. For this reason, each point falling outside the overall range is excluded in the process of calculating the propagation velocity of a shear wave or determined as a point at which the propagation velocity of a shear wave cannot be calculated, and hence is output so as not to be plotted. For this reason, there has been proposed a method of indicating the degree of reliability with respect to the calculated propagation velocity of the shear wave.

If, however, a measurement result such as the propagation velocity of a shear wave has not been output, the operator cannot know a specific reason why the measurement result has not been output. In addition, even if a measurement result such as the propagation velocity of a shear wave is output, the operator cannot specifically know the degree of reliability of the measurement result. Furthermore, if the measurement result is low in reliability, the operator cannot determine whether it is possible to obtain a reliable measurement result by changing the region associated with measurement. The operator therefore randomly sets a region of interest and performs comprehensive determination from an obtained measurement result (numerical value), palpation, and other clinical findings, thereby determining whether the obtained numerical value is valid. As described above, the conventional ultrasonic diagnostic apparatus does not allow the operator to determine the validity of the measurement result obtained by the above technique unless he/she gives certain consideration to the hardness of a tissue in an object in advance.

Demands have arisen for a display method which allows the operator to intuitively and easily grasp the validity of a measurement result even when he/she cannot predict the validity. For example, it suffices if the operator can check how a shear wave as primary information for hardness measurement propagates in an object (e.g., whether the shear wave uniformly propagates in an azimuth (Lateral) direction as expected by the operator, whether the shear wave is reflected or refracted, or whether the shear wave propagates with some kind of tendency). As a method of allowing the operator to check how a shear wave propagates, for example, there is available a method of displaying how a shear wave propagates in the form of a moving image. In clinical practice, however, it takes time to display a moving image for checking the propagation of a shear wave for each measurement and check the propagation of the shear wave. This technique is therefore not practical.

It is an object of this embodiment to provide an ultrasonic diagnostic apparatus which can visualize the propagation of shear waves generated in an object in a form that allows an examiner to easily check.

BRIEF DESCRIPTION OF THE DRAWINGS

FIG. 4 is a flowchart showing a processing procedure concerning a shear wave arrival time image generation function according to the first embodiment.

FIG. 10 is an example of a flowchart showing a processing procedure concerning a shear wave arrival time corrected image generation function according to a modification of the first embodiment.

FIG. 11 is a view showing an example of a corrected shear wave arrival time image together with an example of a shear wave arrival time image according to a modification of the first embodiment.

FIG. 12 is a block diagram showing an example of the arrangement of an ultrasonic diagnostic apparatus according to the second embodiment.

FIG. 13 is an exemplary flowchart showing a procedure for shear wave propagation velocity image generation processing according to the second embodiment.

FIG. 14 is a graph showing an example of temporal changes in displacement in a direction away from an ultrasonic probe at four points on four different scanning lines at the same depth according to the first modification of the second embodiment.

FIG. 15 is a graph showing an example of the relationship between shear wave arrival times and distances from shear wave generation positions at four points on four different scanning lines at the same depth according to the first modification of the second embodiment.

DETAILED DESCRIPTION

Figure 1:
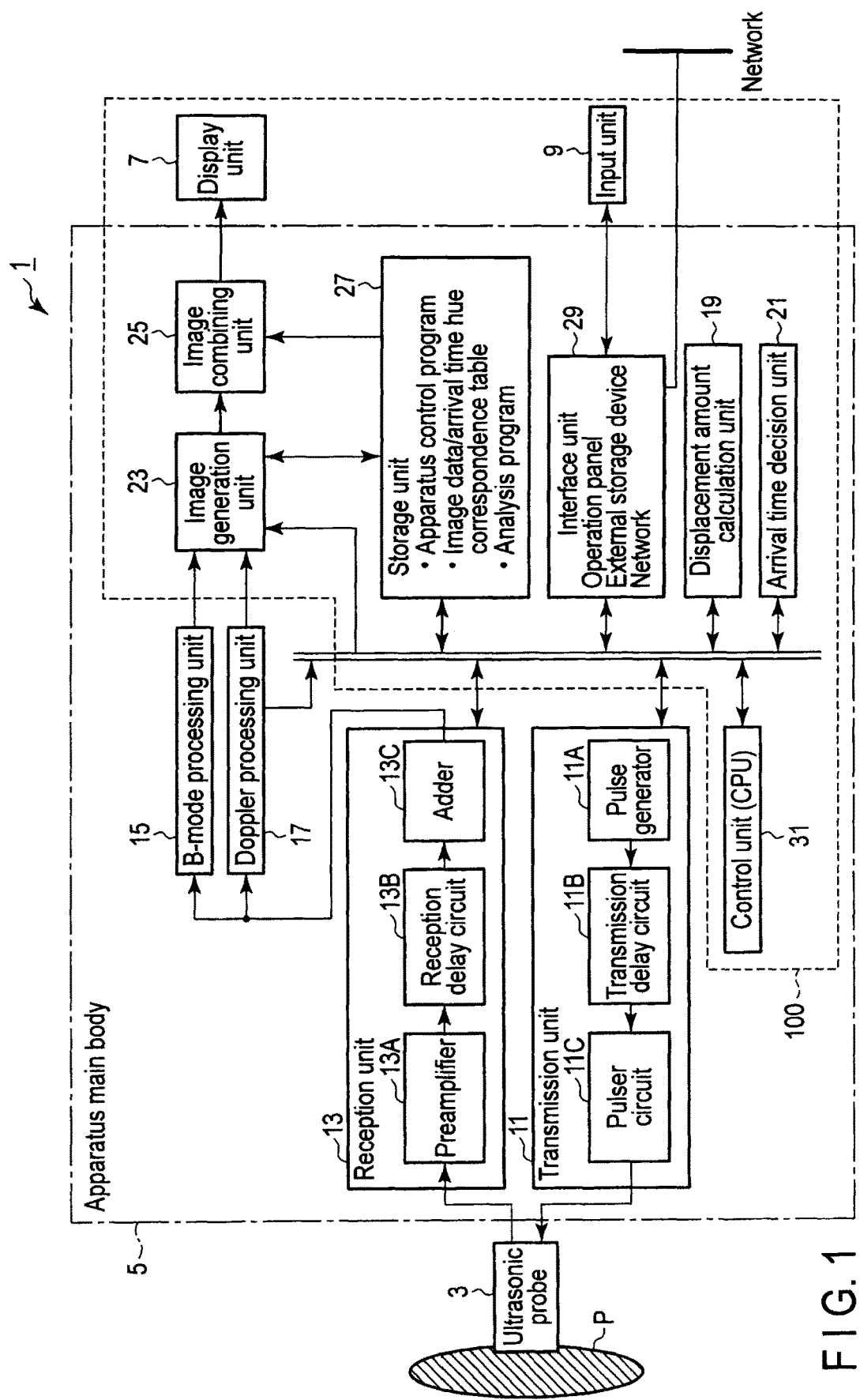
FIG. 1 is a block diagram showing an example of the arrangement of an ultrasonic diagnostic apparatus according to the first embodiment.

In general, according to one embodiment, an ultrasonic diagnostic apparatus includes an ultrasonic probe, a transmission unit, a reception unit, a displacement amount calculation unit, an arrival time decision unit, and an image generation unit. The ultrasonic probe includes a plurality of transducers. The transmission unit is configured to transmit a first ultrasonic wave for generating a shear wave in an object to a first region and transmit a second ultrasonic wave to a second region in the object via the ultrasonic probe. The reception unit is configured to generate a reception signal based on the second ultrasonic wave. The displacement amount calculation unit is configured to calculate a displacement amount of a tissue accompanying propagation of the shear wave to the second region by using the reception signal. The arrival time decision unit is configured to decide an arrival time when the shear wave has arrived at each position in the second region, based on a temporal change in the displacement amount concerning the each position in the second region. The image generation unit is configured to generate, based on the arrival time and pixel values set in advance in accordance with the arrival times, a shear wave arrival time image with the pixel values being assigned in accordance with the arrival times.

The ultrasonic diagnostic apparatus according to an embodiment will be described below with reference to the accompanying drawings. Note that in the following description, the same reference numerals denote constituent elements having almost the same arrangements, and a repetitive description will be made only when required.

First Embodiment

FIG. 1 is a block diagram showing the arrangement of an ultrasonic diagnostic apparatus 1 according to the first embodiment. As shown in FIG. 1, the ultrasonic diagnostic apparatus 1 includes an ultrasonic probe 3, an apparatus main body 5, a display unit 7, and an input unit 9 which is connected to the apparatus main body 5 to input various types of instructions, commands, and information from the operator to the apparatus main body 5. In addition, a biological signal measurement unit (not shown) typified by an electrocardiograph, phonocardiograph, sphygmograph, or respiration sensor and a network may be connected to the ultrasonic diagnostic apparatus 1 via an interface unit 29 (to be described later).

The ultrasonic probe 3 includes a plurality of piezoelectric transducers, a matching layer, and a backing member provided on the rear surface side of the plurality of piezoelectric transducers. The plurality of piezoelectric transducers are reversible acoustic/electric conversion elements such as piezoelectric ceramic elements. The plurality of piezoelectric transducers are juxtaposed and mounted on the distal end of the ultrasonic probe 3. Assume that in the following description, one piezoelectric transducer forms one channel.

Each piezoelectric transducer generates an ultrasonic wave in response to a driving signal supplied from a transmission unit 11 (to be described later). When an ultrasonic wave is transmitted to an object P via the ultrasonic probe 3, the transmitted ultrasonic wave (to be referred to as the transmission ultrasonic wave hereinafter) is reflected by a discontinuity surface of acoustic impedance of a living tissue in the object. Each piezoelectric transducer receives the reflected ultrasonic waves and generates an echo signal. The amplitude of the echo signal depends on an acoustic impedance difference on the discontinuity surface as a boundary concerning the reflection of the ultrasonic wave. The frequency of the echo signal produced when a transmission ultrasonic wave is reflected by a moving blood flow, the surface of the cardiac wall, or the like is subjected to a frequency shift depending on the velocity component of the moving body (the blood flow and the surface of the cardiac wall) in the ultrasonic transmission direction due to the Doppler effect.

The ultrasonic probe 3 will be described below as a probe designed to perform two-dimensional scanning with a one-dimensional array. Note that the ultrasonic probe 3 may be a mechanical four-dimensional probe which executes three-dimensional scanning by swinging a one-dimensional array in a direction perpendicular to the array direction of a plurality of transducers. In addition, the ultrasonic probe 3 is not limited to a mechanical four-dimensional probe, and it is possible to use a two-dimensional array probe.

The matching layer is provided on the ultrasonic emitting surface side of the plurality of piezoelectric transducers to make the transmission/reception of ultrasonic waves efficient with respect to the object P. The backing member prevents ultrasonic waves from propagating backward from the piezoelectric transducers.

The apparatus main body 5 includes the transmission unit 11, a reception 13, a B-mode processing unit 15, a Doppler processing unit 17, a displacement amount calculation unit 19, an arrival time decision unit 21, an image generation unit 23, an image combining unit 25, a storage unit 27, the interface unit 29, and a control unit (central processing unit (to be referred to as a CPU hereinafter)) 31.

The transmission unit 11 includes a pulse generator 11A, a transmission delay circuit 11B, and a pulser circuit 11C. The pulse generator 11A repeatedly generates rate pulses for the formation of transmission ultrasonic waves at a predetermined rate frequency fr Hz (period: 1/fr sec). The generated rate pulses are distributed to channel counts and sent to the transmission delay circuit 11B.

The transmission delay circuit 11B gives each rate pulse a delay time (to be referred to as a transmission delay time hereinafter) necessary to focus a transmission ultrasonic wave into a beam and determine transmission directivity for each of the plurality of channels. The storage unit 27 (to be described later) stores the transmission direction or transmission delay time of transmission ultrasonic waves (to be referred to as a transmission delay pattern hereinafter). The CPU 3 (to be described later) refers to the transmission delay pattern stored in the storage unit 27 at the time of transmission of ultrasonic waves.

The pulser circuit 11C applies a voltage pulse (driving signal) to each transducer of the ultrasonic probe 3 at the timing based on this rate pulse. With this operation, an ultrasonic beam is transmitted to the object.

The transmission of the first ultrasonic wave which generates a shear wave will be described in detail. The transmission unit 11 transmits a push pulse (first ultrasonic wave) which generates a shear wave in an object to the first region via the ultrasonic probe 3. The transmission unit 11 transmits the second ultrasonic wave to the second region (to be described later) before and after the transmission of the first ultrasonic wave. The transmission unit 11 transmits the second ultrasonic wave to obtain the displacement amount of a tissue due to the shear wave generated in the first region. More specifically, the transmission unit 11 transmits a push pulse to a region of interest (to be referred to as an ROI hereinafter) input via the input unit 9 (to be described later) or a region (to be referred to as the first region hereinafter) near the boundary of a predetermined region in the azimuth direction such as a region to which the operator pays attention (to be referred to as a target region) so as to set the depth set in advance as a focal point (to be referred to as a shear wave generation position hereinafter). In other words, a shear wave generation position is set on a scanning line located outside and near a predetermined region. The depth set in advance is, for example, the average depth of a predetermined region.

The frequency of a push pulse is almost equal to that of an ultrasonic wave transmitted in the B mode and the Doppler mode. The wave number of a push pulse is larger than that of an ultrasonic wave transmitted in the B mode and Doppler mode. More specifically, the transmission unit 11 causes the CPU 31 (to be described later) to read out, from the storage unit 27, a transmission delay pattern (to be referred to as a shear wave generation transmission delay pattern hereinafter) for focusing ultrasonic waves into a beam at the midpoint of the first region in the depth direction. The transmission delay circuit 11B gives each rate pulse a transmission delay time according to the shear wave generation delay pattern. At the timing based on this rate pulse, the pulser circuit 11C applies, for each transducer, a driving signal for generating a push pulse.

The transmission unit 11 transmits the second ultrasonic wave to a predetermined region (second region) before and after the transmission of the first ultrasonic wave.

The reception unit 13 includes a preamplifier 13A, an analog to digital (to be referred to as A/D hereinafter) converter (not shown), a reception delay circuit 13B, and an adder 13C. The reception unit 13 generates a reception signal based on reflected waves originating from the second ultrasonic wave and the shear wave.

The preamplifier 13A amplifies an echo signal from the object P, captured via the ultrasonic probe 3, for each channel. The A/D converter converts the amplified reception echo signal into a digital signal.

The reception delay circuit 13B gives the reception echo signal converted into the digital signal a delay time necessary to decide reception directivity (to be referred to as a reception delay time hereinafter). The storage unit 27 (to be described later) stores the reception direction or reception delay time (to be referred to as a reception delay pattern hereinafter) of an echo signal. The CPU 31 (to be described later) refers to the reception delay pattern stored in the storage unit 27. The adder 13C adds a plurality of echo signals given delay times. With this addition, the reception unit 13 generates a reception signal (to be also referred to as an RF (radiofrequency) signal) whose reflection component from a direction corresponding to the reception directivity is enhanced. The transmission directivity and the reception directivity determine the comprehensive directivity of ultrasonic transmission/reception. This comprehensive directivity determines an ultrasonic beam (so-called "ultrasonic scanning line"). More specifically, the reception unit 13 receives the reflected wave of the second ultrasonic wave concerning the physical tissue displacement caused by a shear wave.

The B-mode processing unit 15 includes an envelope detector and a logarithmic converter (neither of which is shown). The envelope detector performs envelope detection of the reception signal output from the reception unit 13. The envelope detector outputs the envelope-detected signal to the logarithmic converter (to be described later). The logarithmic converter relatively enhances a weak signal by logarithmically converting the envelope-detected signal. The B-mode processing unit 15 generates a signal value (B-mode data) for each depth on each scanning line or in each ultrasonic transmission/reception based on the signal enhanced by the logarithmic converter.

If the ultrasonic probe 3 is a mechanical four-dimensional probe or two-dimensional probe, the B-mode processing unit 15 may generate three-dimensional B-mode data having a plurality of signal values respectively arranged in the azimuth direction, elevation direction, and depth direction (to be referred to as the range direction hereinafter) in a scanned region. The range direction is the depth direction on a scanning line. The azimuth direction is, for example, an electronic scanning direction along the array direction of one-dimensional ultrasonic transducers. The elevation direction is the mechanical swinging direction of the one-dimensional ultrasonic transducers. Note that three-dimensional B-mode data may be data obtained by arranging a plurality of pixel values, a plurality of luminance values, or the like in the azimuth direction, elevation direction, and range direction, respectively, along scanning lines. In addition, three-dimensional B-mode data may be data concerning an ROI set in advance in a scanned region. The B-mode processing unit 15 may generate volume data instead of three-dimensional B-mode data. The date generated by the B-mode processing unit 15 will be collectively referred to as B-mode data.

The Doppler processing unit 17 includes a mixer, low pass filter (to be referred to as an LPF hereinafter), and velocity/variance/power computation device (none of which are shown). The mixer multiplies the reception signal output from the reception unit 17 by a reference signal having a frequency $f_0$ equal to the transmission frequency. This multiplication obtains a signal having a component with a Doppler shift frequency $f_d$ and a signal having a frequency component of $(2f_0+f_d)$. The LPF removes a signal of a high-frequency component $(2f_0+f_d)$ from a signal having two types of frequency components from the mixer. The Doppler processing unit 142 generates a Doppler signal having the component with the Doppler shift frequency $f_d$ by removing the signal of the high-frequency component $(2f_0+f_d)$.

Note that the Doppler processing unit 17 may use a quadrature detection scheme to generate Doppler signals. In this case, the Doppler processing unit performs quadrature detection to convert a reception signal (RF signal) into an IQ signal. The Doppler processing unit 142 generates a Doppler signal having the Doppler shift frequency $f_d$ by performing complex Fourier transform for the IQ signal. Doppler signals are, for example, Doppler components caused by a blood flow, tissue, and contrast medium.

The velocity/variance/power computation device includes an MTI (Moving Target Indicator) filter, LPF filter, and autocorrelation computation device (neither of which is shown). Note that the apparatus may include a cross-correlation computation device instead of an autocorrelation computation device. The MTI filter removes a Doppler component (a clutter component) caused by the respiratory movement or pulsatory movement of an organ or the like from a generated Doppler signal. The MTI filter is used to extract a Doppler component (to be referred to as a blood flow Doppler component hereinafter) concerning a blood flow from a Doppler signal. The LPF is used to extract a Doppler component (to be referred to as a tissue Doppler component hereinafter) concerning the movement of a tissue from a Doppler signal.

The autocorrelation computation device calculates an autocorrelation value concerning a blood flow component and a tissue Doppler component. The autocorrelation computation device calculates the average flow velocity value, a variance, the reflection intensity (power) of the Doppler signal, and the like based on the calculated autocorrelation value. The velocity/variance/power computation device generates color Doppler data at each position in a predetermined region based on the average velocity value, the variance, the reflection intensity of the Doppler signal, and the like based on a plurality of Doppler signals. Doppler signals and color Doppler data will be collectively referred to as Doppler data hereinafter.

The following will describe the processing of calculating the phase difference between tissue Doppler components (to be referred to as autocorrelation processing hereinafter) by using the autocorrelation computation device. First of all, the unit transmits and receives ultrasonic waves in one scanning line direction at a predetermined pulse repetition frequency (to be referred to as a PRF hereinafter) over a plurality of times (n times). The reception unit 13 then generates a plurality of reception signals (n signals). The unit extracts a plurality of tissue Doppler components from a plurality of Doppler signals respectively corresponding to a plurality of reception signals. The unit adds, to a tissue Doppler component, a depth in one scanning line direction and a number indicating a transmission/reception count as additional information.

The autocorrelation computation device executes autocorrelation processing for a plurality of reception signals (n signals) at the same depth in one scanning line direction. More specifically, the autocorrelation computation device calculates the phase difference between tissue Doppler components based on the ith ($1 \leq i \leq n-1$) tissue Doppler component TD(i) and the (i+1)th ($2 \leq i+1 \leq n$) tissue Doppler component TD(i+1). More specifically, the autocorrelation computation device calculates the phase difference between TD(i) and TD(i+1) by executing complex Fourier transform for a complex conjugate product TD(i)×TD*(i+1) between TD(i) and TD(i+1). The autocorrelation computation device repeats this procedure for calculating a phase difference from i=1 to i=n−1. That is, the autocorrelation computation device calculates (n−1) phase differences for each 1/PRF and depth by using the n reception signals generated by n times of ultrasonic transmission/reception in one scanning line direction. Note that the autocorrelation computation device may calculate phase differences every time a tissue Doppler component is generated. A phase difference corresponds to the displacement amount of a tissue for each 1/PRF and depth. Integrating the first to ith phase differences can obtain the displacement amount of the ith tissue with reference to the first tissue Doppler component. Instead of integrating the phase differences from first to ith phase differences, it is possible to directly calculate the phase difference between TD(1) and TD(j).

Note that a cross-correlation computation device (not shown) may calculate phase differences by cross-correlation processing instead of autocorrelation processing. Cross-correlation processing is, for example, the processing of calculating the phase differences between the tissue Doppler component obtained by the first ultrasonic transmission/reception and the tissue Doppler components obtained by second and subsequent ultrasonic transmissions/receptions. That is, cross-correlation processing is the processing of calculating phase differences with reference to the tissue Doppler component obtained by the first ultrasonic transmission/reception.

The cross-correlation computation device executes cross-correlation processing for a plurality of reception signals (n signals) at the same depth in one scanning line direction. More specifically, the cross-correlation computation device calculates the time lag between tissue Doppler components based on a first tissue Doppler component TD(1) and a jth ($2 \leq j \leq n$) tissue Doppler component TD(j). The cross-correlation computation device repeats this procedure for calculating a phase difference from j=2 to j=n. That is, the cross-correlation computation device calculates (n−1) time lag for each 1/PRF and depth with respect to the n times of ultrasonic transmission/reception in one scanning line direction. The time lag obtained by the cross-correlation computation device indicates the time lag of the jth tissue Doppler component with reference to the first tissue Doppler component. That is, the time lag output from the cross-correlation computation device represents the displacement amount of the tissue with reference to the first tissue Doppler component.

The displacement amount calculation unit 19 approximates a displacement amount of a tissue concerning the body movement of an object (to be referred to as a body movement displacement amount hereinafter) for each depth in the second region based on the displacement amount (to be referred to as the first displacement data hereinafter) of the tissue obtained by the autocorrelator before the transmission of a push pulse and the displacement amount of the tissue immediately before the end of the nth ultrasonic transmission/reception (nth, (n−1)th, or the like) of the displacement amounts (to be referred to as the second displacement data hereinafter) of the tissues obtained by the autocorrelation computation device after the transmission of the push pulse. The displacement amount calculation unit 19 calculates the displacement amount of the tissue accompanying the propagation of a shear wave (to be referred to as shear wave propagation data hereinafter) by subtracting the approximated body movement displacement amount from the first and second displacement data. Note that shear wave propagation data may be the displacement amount of the tissue in a direction away from the ultrasonic probe 3 along a scanning line direction.

For a concrete description, assume that the number of times of execution of ultrasonic transmission/reception (to be referred to as a pre-push pulse transmission/reception count hereinafter) for one scanning line in a predetermined region before the transmission of a push pulse is 15. Assume also that a number n of times of execution of ultrasonic transmission/reception (to be referred to as a post-push pulse transmission/reception count hereinafter) for one scanning line in a predetermined region after the transmission of a push pulse is 65.

More specifically, the displacement amount calculation unit 19 approximates a temporal change in body movement displacement amount with, for example, a second-order polynomial over an ultrasonic transmission/reception period concerning the first and second displacement data based on the first displacement data concerning the pre-push pulse transmission/reception count (15) and a plurality of displacement amounts respectively corresponding to the 64th and 65th transmission/reception of the post-push pulse transmission/reception count (65). Data representing a temporal change in body movement displacement amount will be referred to as body movement displacement data hereinafter. Body movement displacement data is generated for each position in a predetermined region (i.e., for each scanning line and depth in the predetermined region). The displacement amount calculation unit 19 calculates shear wave propagation data representing a temporal change in the displacement amount of the tissue by a shear wave by subtracting the body movement displacement data from the first and second displacement data. Shear wave propagation data is generated for each position in a predetermined region. The displacement amount calculation unit 19 outputs the shear wave propagation data to the arrival time decision unit 21 (to be described later). The displacement amount calculation unit 19 calculates shear wave propagation data corresponding to each position in a predetermined region by the above processing.

The arrival time decision unit 21 decides the arrival time of a shear wave (to be referred to as a shear wave arrival time hereinafter) which has arrived at each position in a predetermined region, based on a temporal change in the displacement amount of a tissue in shear wave propagation data. More specifically, the arrival time decision unit 21 decides, as a shear wave arrival time, the time corresponding to the maximum value of the displacement amount of a tissue in shear wave propagation data with respect to each position in a predetermined region, with the transmission start or end time of a push pulse being time 0. The arrival time decision unit 21 outputs data concerning the arrival time (to be referred to as arrival time data hereinafter) at each position in a predetermined region to the image generation unit 23 (to be described later).

Note that the arrival time decision unit 21 may decide, as a shear wave arrival time, the time corresponding to the maximum temporal change of temporal changes in the displacement amount of a tissue in shear wave propagation data. The arrival time decision unit 21 may also decide, as a shear wave arrival time, the time corresponding to the maximum value of the displacement amount of a tissue in shear wave propagation data, with the time shifted from the transmission start or end time of a push pulse as a reference by a predetermined time being 0.

Note that the arrival time decision unit 21 may decide an arrival time based on the maximum displacement amount of the maximal values of temporal changes in the displacement amount of a tissue in shear wave propagation data. More specifically, the arrival time decision unit 21 extracts one of temporal changes in the displacement amount of a tissue in shear wave propagation data which takes a maximal value. If, for example, the waveform of shear wave propagation data has a plurality of peaks, there are a plurality of points taking maximal values. The arrival time decision unit 21 extracts one of these maximal values which has the maximum displacement amount. The arrival time decision unit 21 decides an arrival time based on the displacement amount having this maximal value.

The image generation unit 23 includes a digital scan converter (not shown) (to be referred to as a DSC hereinafter) and an image memory. The image generation unit 23 executes coordinate conversion processing (resampling) for the DSC. Coordinate conversion processing is the processing of converting, for example, a scanning line signal string for ultrasonic scanning, which is formed from B-mode data, Doppler data, and arrival time data, into a scanning line signal string in a general video format typified by a TV format. The image generation unit 23 generates an ultrasonic image as a display image by coordinate conversion processing. More specifically, the image generation unit 23 generates a B-mode image based on B-mode data. The image generation unit 23 generates a Doppler image such as an average velocity image, variance image, or power image based on Doppler data.

The image generation unit 23 generates a shear wave arrival time image with hues being assigned in accordance with arrival times at the respective positions in a predetermined region, based on arrival time data and the arrival time hue correspondence table stored in the storage unit 27 (to be described later). The arrival time hue correspondence table is the correspondence table of hues corresponding to arrival time values. For example, a hue corresponding to an arrival time of 0 is blue. For example, hues are sequentially defined as blue, blue-green, green, yellow-green, yellow, orange, and red in ascending order of arrival time, with the maximum arrival time corresponding to red. Although this embodiment has exemplified the case in which hues are assigned, parameters to be assigned are not limited to hues, and any types of parameters can be used as long as they are used to define pixel values. When, for example, generating a grayscale shear wave arrival time image, it is also possible to generate a grayscale shear wave arrival time image by assigning monochrome luminance values to an arrival time hue correspondence table instead of hues and assigning luminance values at the respective positions in a predetermined region in accordance with arrival times.

The image memory stores data (to be referred to as image data hereinafter) corresponding to generated ultrasonic images (B-mode images, average velocity images, variance images, power images, and shear wave arrival time images). The image data stored in the image memory is read out in accordance with an instruction from the operator via the input unit 9 (to be described later). The image memory is, for example, a memory which stores ultrasonic images corresponding to a plurality of frames immediately before freezing. Continuously displaying (cine displaying) the images stored in this cine memory can display a moving ultrasonic image on the display unit 7 (to be described later).

The image combining unit 25 combines an ultrasonic image with the character information of various parameters, scale marks, and the like. The image combining unit 25 outputs the combined ultrasonic image to the display unit 7 (to be described later). The image combining unit 25 generates a superimposed image by superimposing a shear wave arrival time image on a B-mode image upon alignment. The image generation unit 23 outputs the generated superimposed image to the display unit 7.

The storage unit 27 stores pluralities of reception delay patterns, transmission delay patterns, and shear wave generation transmission delay patterns with different focus depths, control programs for the ultrasonic diagnostic apparatus 1, a diagnostic protocol, various data groups such as transmission/reception conditions, diagnosis information (patient IDs, findings by doctors, and the like), the reception signals generated by the reception unit 13, the B-mode data generated by the B-mode processing unit 15, the Doppler data generated by the Doppler processing unit 17, first and second displacement data at each position in a predetermined region, body movement displacement data, shear wave propagation data, arrival time data, arrival time hue correspondence tables, B-mode images, average velocity images, variance images, power images, shear wave arrival time images, and an algorithm concerning the generation of shear wave arrival time images (to be referred to as a shear wave arrival time image generation algorithm hereinafter). Note that the above image memory may be provided in the storage unit 27.

The interface unit 29 is an interface concerning the input unit 9, a network, an external storage device (not shown), and a biological signal measurement unit (not shown). Data such as ultrasonic images, analysis results, and the like obtained by the apparatus main body 5 can be transferred to other apparatuses via the interface unit 29 and the network. Note that the interface unit 29 can also download the medical images concerning the object which are acquired by other medical image diagnostic apparatuses (not shown) via the network.

The CPU 31 reads out a transmission delay pattern, reception delay pattern, shear wave generation transmission delay pattern, and apparatus control program stored in the storage unit 27, based on the selection between the B mode, the Doppler mode, and the shear wave arrival time image display mode, frame rate, scan depth, and transmission start/end which are input by the operator via the input device 9, and controls the apparatus main body 5 in accordance with these piece of information. For example, the CPU 31 reads out the shear wave arrival time image generation algorithm from the storage unit 27. The CPU 31 controls the transmission 11, the Doppler processing unit 17, the displacement amount calculation unit 19, and the arrival time decision unit 21 in accordance with the readout shear wave arrival time image generation algorithm. The shear wave arrival time image display mode is the mode of generating a shear wave arrival time image and displaying the image.

More specifically, upon receiving the shear wave arrival time image display mode via the display unit 7, the CPU 31 controls the transmission unit 11 to transmit ultrasonic waves in the scanning line direction in a predetermined region to obtain the first displacement data. The CPU 31 controls the Doppler processing unit 17 to generate the first displacement data.

The CPU 31 then outputs the shear wave generation transmission delay pattern read out from the storage unit 27 to the transmission unit 11 to generate a push pulse. The CPU 31 controls the transmission unit 11 to transmit ultrasonic waves for obtaining the second displacement data in the scanning line direction in a predetermined region. The CPU 31 controls the Doppler processing unit 17 to generate the second displacement data. The CPU 31 controls the displacement amount calculation unit 19 to generate body movement displacement data, based on the first and second displacement data. The CPU 31 controls the displacement amount calculation unit 19 to generate shear wave propagation data, based on the first and second displacement data and the body movement displacement data. The CPU 31 controls the arrival time decision unit 21 to generate arrival time data, based on the shear wave propagation data. The CPU 31 controls the image generation unit 23 to generate a shear wave arrival time image, based on the arrival time hue correspondence table and arrival time data read out from the storage unit 27.

The display unit 7 displays ultrasonic images such as a B-mode image and a Doppler image, a shear wave arrival time image, a superimposed image, and the like based on outputs from the image combining unit 25. Note that the display unit 7 may execute adjustments concerning brightness, contrast, dynamic range, γ correction, and the like and color mapping for a displayed image.

The input unit 9 is connected to the interface unit 29 and inputs various instructions, commands, information, selections, and settings from the operator to the apparatus main body 5. The input unit 9 includes input devices such as a trackball, switch buttons, mouse, and keyboard (none of which are shown). The input device detects the coordinates of a cursor displayed on the display screen, and outputs the detected coordinates to the CPU 31. Note that the input device may be a touch command screen provided to cover the display screen. In this case, the input unit 9 detects touched and designated coordinates by a coordinate reading principle such as an electromagnetic induction scheme, magnetostriction scheme, or a pressure-sensitive scheme, and outputs the detected coordinates to the CPU 31. When, for example, the operator operates the end button or freeze button of the input unit 9, the ultrasonic transmission/reception is terminated, and the apparatus main body 5 is set in a pause state.

The input unit 9 inputs a region of interest or a predetermined region to which the operator pays attention in accordance with an instruction from the operator. The input unit 9 inputs the mode selected in accordance with an instruction from the operator.

(Displacement Amount Observation Scanning Function)

The displacement amount observation scanning function is a function concerning a scanning procedure for acquiring the displacement amount of a tissue accompanying the propagation of a shear wave. Processing (to be referred to as displacement amount observation scanning processing hereinafter) concerning the displacement amount observation scanning function will be described below.

Figure 2:
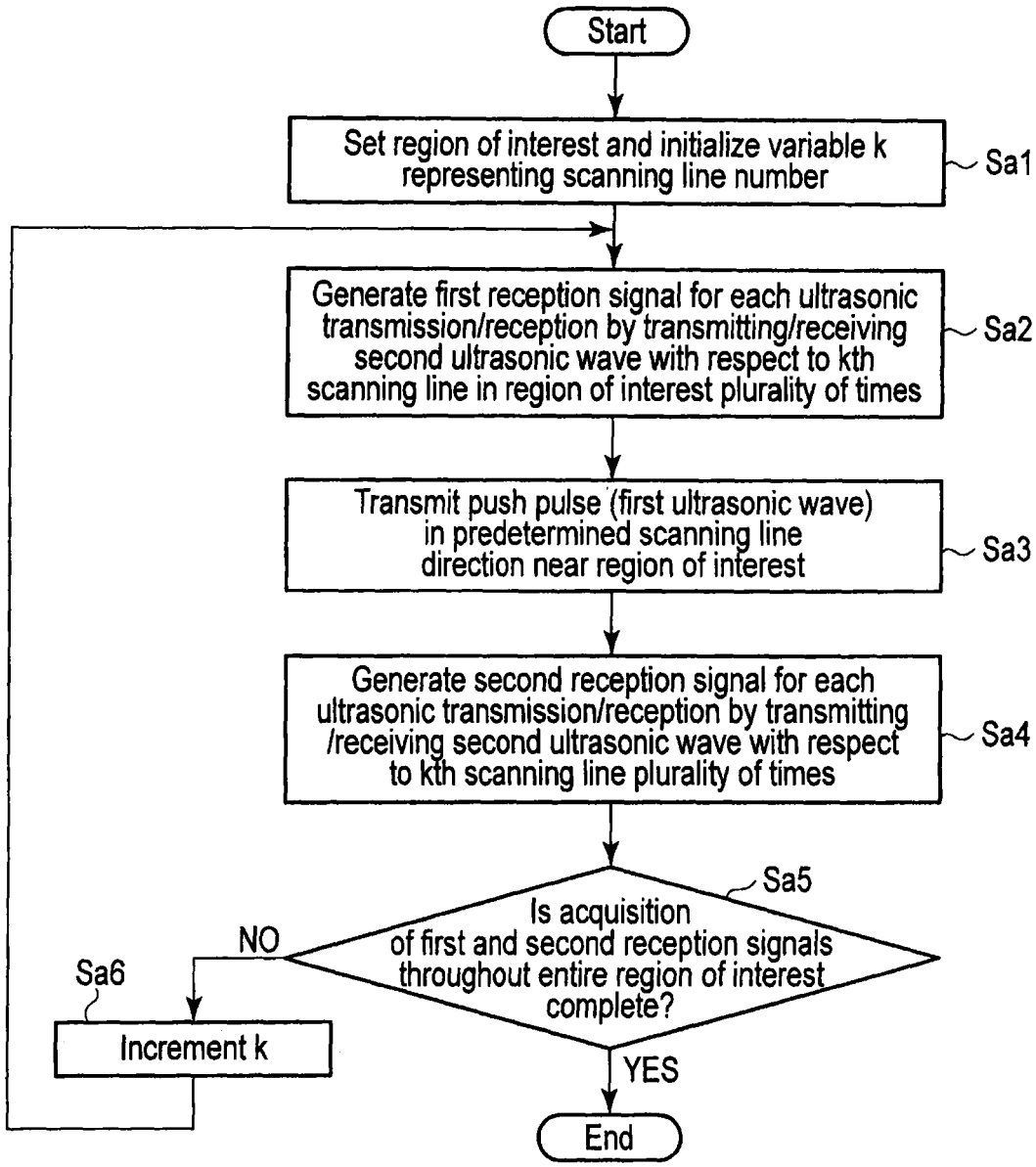
FIG. 2 is a flowchart showing a processing procedure concerning a displacement amount observation scanning function according to the first embodiment.
Figure 3:
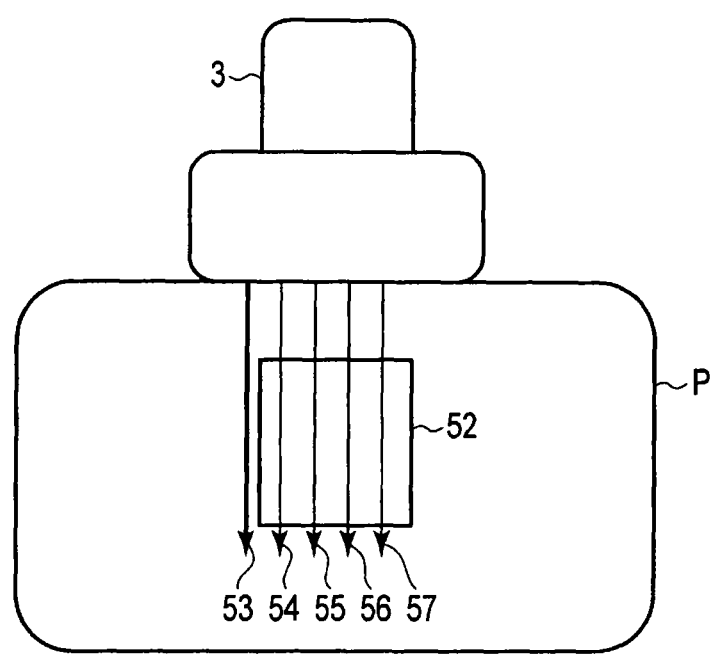
FIG. 3 is a view showing scanning lines concerning the first ultrasonic wave for generating a shear wave and scanning lines concerning the second ultrasonic wave for obtaining the first and second reception signals, together with a region of interest, according to the first embodiment.

FIG. 2 is a flowchart showing a procedure for displacement amount observation scanning processing. FIG. 3 is a schematic view schematically showing, together with a region of interest (or target region) 52, a scanning line (to be referred to as a shear wave generation scanning line hereinafter) 53 for generating a shear wave and scanning lines (to be referred to as observation scanning lines hereinafter) 54, 55, 56, and 57 concerning ultrasonic transmission/reception for observing the tissue displacement amount caused by a shear wave in displacement amount observation scanning processing.

Before the transmission of ultrasonic waves to the object P, the apparatus sets the region of interest 52 in accordance with an instruction from the operator via the input unit 9 (step Sa1). At this time, the apparatus initializes a variable k representing the number of an observation scanning line. Note that the apparatus may set a region to which the operator pays attention instead of the region of interest 52. The apparatus transmits/receives the second ultrasonic wave a plurality of times (e.g., 15 times) in the kth scanning line (e.g., the line 54) in the region of interest 52 to generate the first reception signal for each ultrasonic transmission/reception (step Sa2). The apparatus then reads out a shear wave generation transmission delay pattern from the storage unit 27 based on the position of the region of interest 52. The apparatus transmits a push pulse (first ultrasonic wave) along the predetermined scanning line 53 near the region of interest 52 by using the readout shear wave generation transmission delay pattern (step Sa3). After the transmission of the push pulse, the apparatus transmits/receives an ultrasonic wave (second ultrasonic wave) a plurality of times (e.g., 65 times) along the kth scanning line (e.g., the line 54) to generate the second reception signal for each ultrasonic transmission/reception (step Sa4). If the first and second reception signals have not been generated throughout the entire region of interest, i.e., throughout the scanning lines 55 to 57 (step Sa5), the apparatus increments k (step Sa6). Thereafter, the apparatus repeats the processing in steps Sa2 to Sa4.

Displacement amount observation scanning processing is the processing of repeatedly performing ultrasonic transmission/reception for the generation of the first reception signal before the transmission of a push pulse, for each of a plurality of observation scanning lines in the region of interest 52, transmitting a push pulse, and performing ultrasonic transmission/reception for the generation of the second reception signal after the transmission of the push pulse. That is, displacement amount observation scanning processing is the scanning processing of executing ultrasonic transmission/reception along one scanning line with one push pulse. Note that the apparatus may execute ultrasonic transmission/reception for a plurality of scanning lines after the transmission of one push pulse. Alternatively, the apparatus may execute so-called parallel simultaneous reception of transmitting an ultrasonic wave once after the transmission of one push pulse and then executing reception in a plurality of scanning line directions.

(Shear Wave Arrival Time Image Generation Function)

The shear wave arrival time image generation function is a function of generating a shear wave arrival time image representing the shear wave arrival times at the respective positions in a predetermined region by hues. Processing (to be referred to as shear wave arrival time image generation processing hereinafter) concerning the shear wave arrival time image generation function will be described below.

FIG. 4 is a flowchart showing an example of a procedure for shear wave arrival time image generation processing.

The apparatus executes autocorrelation processing by using a plurality of first reception signals generated by a plurality of times of ultrasonic transmission/reception for one scanning line before the transmission of a push pulse. The apparatus generates the first displacement data concerning each position in a predetermined region by autocorrelation processing (step Sb1). The apparatus executes autocorrelation processing by using a plurality of second reception signals generated by a plurality of times of ultrasonic transmission/reception for one scanning line after the transmission of the push pulse. The apparatus generates the second displacement data concerning each position in the predetermined region (step Sb2).

Figure 5:
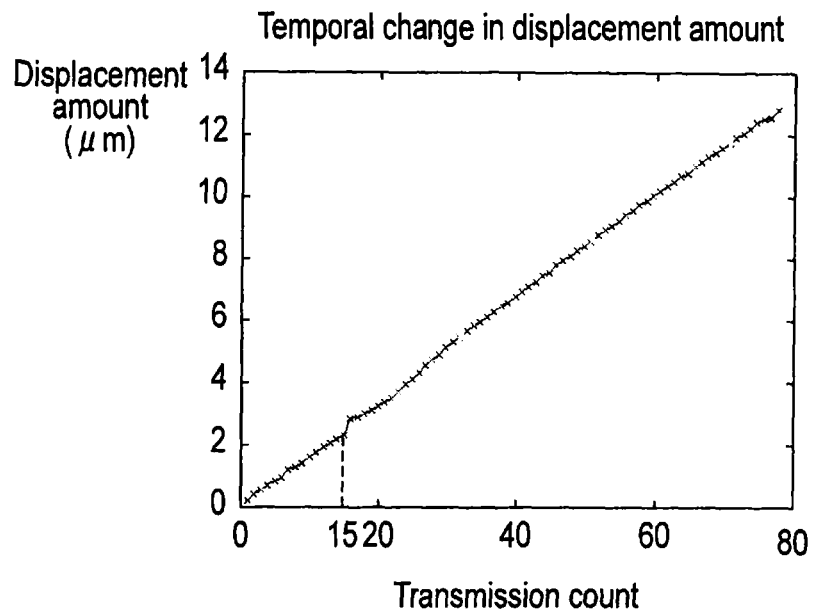
FIG. 5 is a graph showing an example of a temporal change in the displacement amount of a tissue at a given position in a region of interest according to the first embodiment.

FIG. 5 is a graph showing an example of a temporal change in the displacement amount of a tissue at a given position in a region of interest. That is, FIG. 5 is a graph collectively showing the first and second displacement data at a given position in the region of interest. The abscissa in FIG. 5 corresponds to the transmission count of an ultrasonic wave excluding a push pulse. The ordinate in FIG. 5 represents the displacement amount of a tissue. The displacement amounts of a tissue which correspond to transmission counts of 1 to 15 correspond to the first displacement data. The displacement amounts of a tissue which correspond to transmission counts of 16 to 80 correspond to the second displacement data. The displacement amounts in FIG. 5 are those with reference to the displacement amount of the tissue which corresponds to the transmission count of the first ultrasonic wave. That is, the displacement amounts in FIG. 5 correspond to the integrated values of phase differences generated by autocorrelation processing or the time lags generated by cross-correlation processing.

FIG. 5 shows that the tissue moves at an almost constant velocity in one direction (a direction to approach the ultrasonic probe 3) upon the body movement of the object. The body movement of the object makes it impossible to identify the displacement of the tissue due to the propagation of a shear wave.

The apparatus generates body movement displacement data representing the body movement displacement amount of the object based on the displacement amount of the tissue, of the first and second displacement data, which is obtained at the last moment of the nth ultrasonic transmission/reception (e.g., the nth or (n−1)th ultrasonic transmission/reception) (step Sb3). The apparatus generates shear wave propagation data representing a temporal change in the tissue displacement amount caused by a shear wave by subtracting the body movement displacement data from the first and second displacement data (step Sb4). The apparatus decides the shear wave arrival time when a shear wave from the shear wave generation position has arrived at each position in a region of interest corresponding to the shear wave propagation data, based on the shear wave propagation data (step Sb5).

Figure 6:
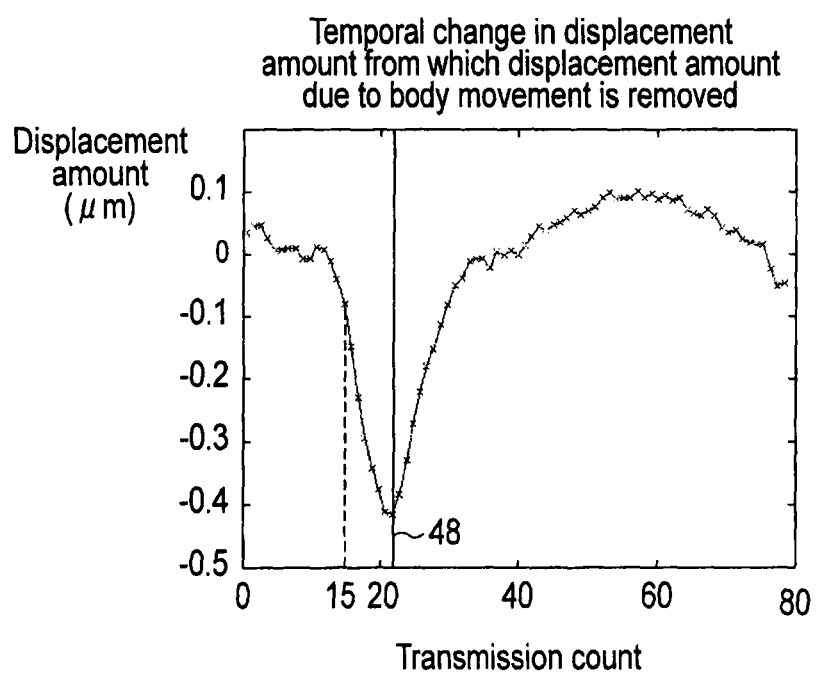
FIG. 6 is a graph showing an example of a temporal change in displacement amount from which the displacement amount of a tissue due to the body movement of an object is removed at a given position in a region of interest according to the first embodiment.

FIG. 6 is a graph showing an example of a temporal change in displacement amount (shear wave propagation data) which is obtained by removing the displacement amount caused by the body movement of the object from the displacement amount of the tissue shown in FIG. 5. The abscissa in FIG. 6 corresponds to the transmission count of an ultrasonic wave excluding a push pulse. The ordinate in FIG. 6 shows the displacement amount of the tissue. The scale marks and sign on the ordinate in FIG. 6 differ from those on the ordinate in FIG. 5. That is, the ordinate in FIG. 6 indicates a direction away from the ultrasonic probe, and the sign on the ordinate is negative which is reverse to that on the ordinate in FIG. 5. In addition, the order of the tissue displacement amount caused by a shear wave differs from the order of the tissue displacement amount caused by body movement.

As shown in FIG. 6, the displacement amount of the tissue is maximum in absolute value after the passage of a shear wave (near the 22nd transmission/reception). Referring to FIG. 6, the arrival time decision unit 21 decides, as a shear wave arrival time, the time (transmission count) corresponding to 48 in FIG. 6 at which the displacement amount of the tissue becomes maximum in absolute value. Note that when deciding, as a shear wave arrival time, the time when a temporal change in the displacement amount of the tissue is negative and maximum, the arrival time decision unit 21 decides a time near a transmission count of 16 as a shear wave arrival time.

Figure 7:
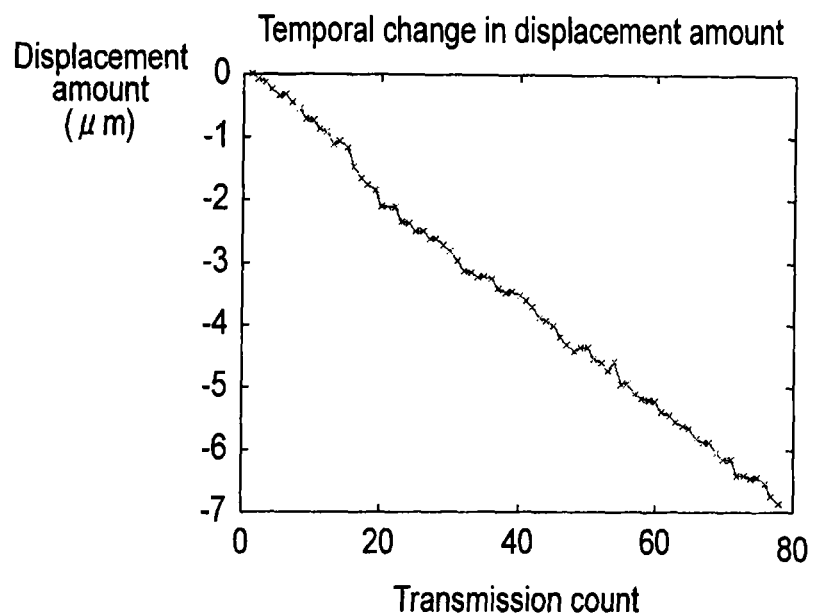
FIG. 7 is a graph showing an example of a temporal change in the displacement amount of a tissue at a given position in a region of interest according to the first embodiment.

FIG. 7 is a graph showing an example of a temporal change in the displacement amount of the tissue at a given position in a region of interest which is different from that in FIG. 5. The ordinate in FIG. 7 indicates a direction away from the ultrasonic probe. The sign on the ordinate is negative which is reverse to that on the ordinate in FIG. 5. FIG. 7 shows that the tissue moves at an almost constant velocity in one direction (a direction away from the ultrasonic probe 3) due to the body movement of the object. The body movement of the object makes it impossible to identify the displacement of the tissue due to the propagation of a shear wave.

Figure 8:
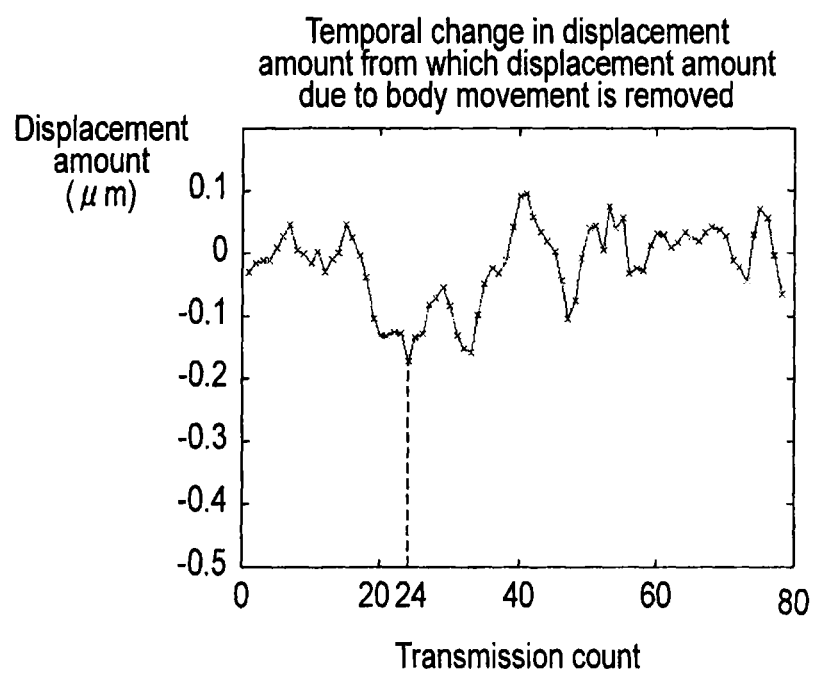
FIG. 8 is a graph showing an example of a temporal change in displacement amount from which the displacement amount of a tissue due to the body movement of an object is removed at a given position in a region of interest according to the first embodiment.

FIG. 8 is a graph showing an example of a temporal change in displacement amount (shear wave propagation data) which is obtained by removing the displacement amount caused by the body movement of the object from the displacement amount of the tissue shown in FIG. 7. The ordinate and abscissa in FIG. 8 are the same as those in FIG. 6. FIG. 8 shows an example of the shear wave propagation data generated when the tissue displacement amount caused by a shear wave is too small or the tissue displacement amount caused by the body movement of the object is irregular at the position at which the shear wave propagation data is obtained. The arrival time decision unit 21 decides a time near a transmission count of 24 as a shear wave arrival time. Unlike the graph of FIG. 6, the graph of FIG. 8 does not explicitly show the shear wave arrival times. When shear wave propagation data like that shown in FIG. 8 is obtained, the resultant shear wave arrival time image exhibits, for example, hues greatly different from those around the image.

The apparatus generates a shear wave arrival time image with hues being assigned in accordance with the shear wave arrival times, based on the decided shear wave arrival times and the arrival time hue correspondence table (step Sb6). The apparatus superimposes the generated shear wave arrival time image on a B-mode image and displays the resultant image on the display unit 7.

Figure 9:
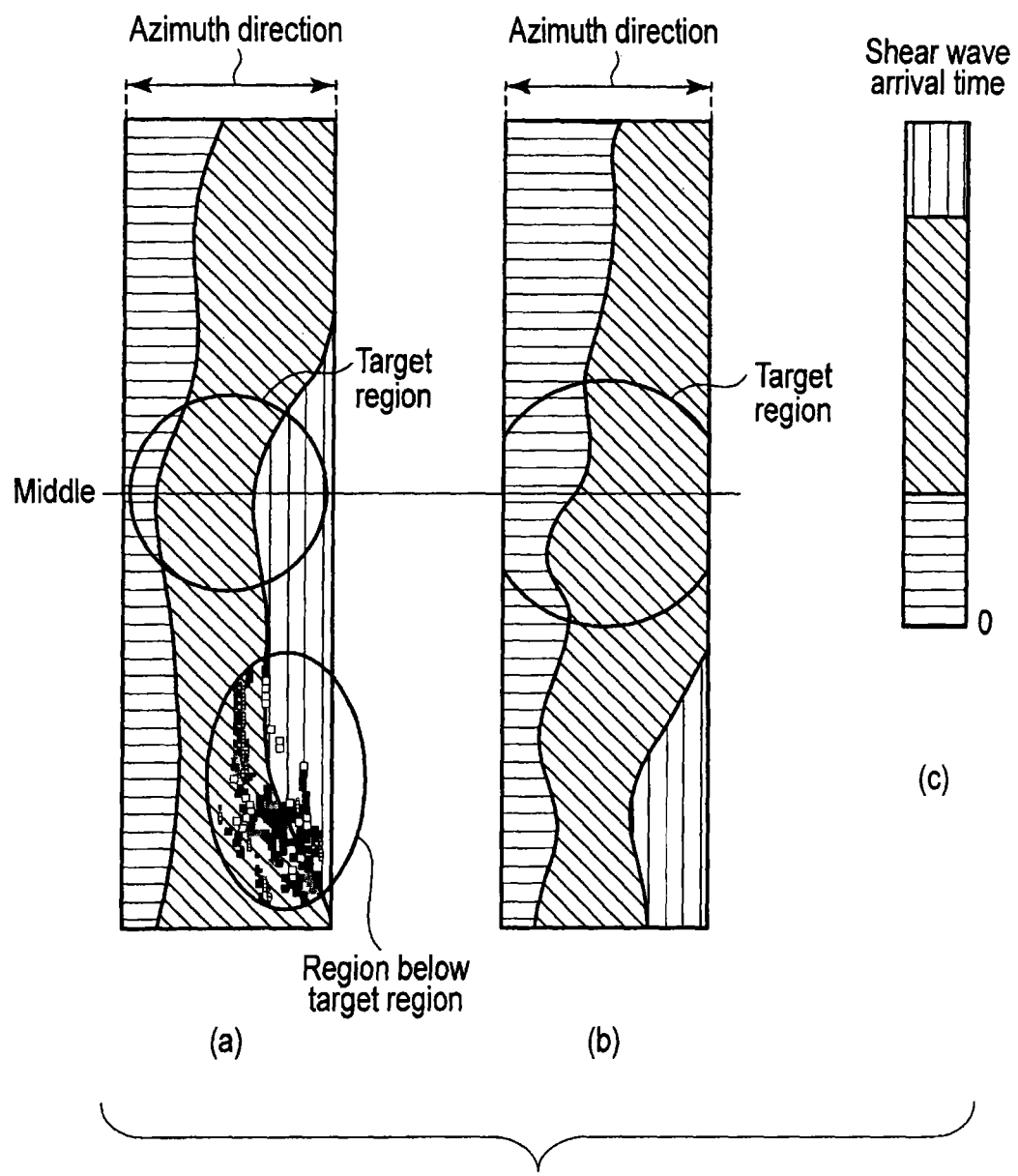
FIG. 9 is a view showing an example of a generated shear wave arrival time image together with an example of a color map showing the legend of hues corresponding to shear wave arrival times according to the first embodiment.

FIG. 9 is a view showing an example of a generated shear wave arrival time image together with an example of a color map showing the legend of hues corresponding to the shear wave arrival times. In FIG. 9, (a) and (b) each show an example of a superimposed image obtained by superimposing a shear wave arrival time image on a B-mode image. The circles in (a) an (b) in FIG. 9 indicate target regions (targets). In FIG. 9, (c) shows a legend of a color map in (a) and (b) in FIG. 9.

The target region in (a) in FIG. 9 indicates a region having a tissue softer than a tissue around the target region. The target region in (b) in FIG. 9 indicates a region having a tissue harder than a tissue around the target region. In both (a) and (b) in FIG. 9, changes in hue in the azimuth direction (changes in grayscale because of monochromatic) indicate how shear waves propagate from left to right when facing the drawing surface. In (a) in FIG. 9, a patchy pattern (mosaic pattern) is displayed in a region below the target region. Referring to (a) in FIG. 9, the region below the target region indicates a region in which the shear wave arrival times have not been accurately evaluated as shown in, for example, FIG. 8. Comparing (a) and (b) in FIG. 9 will reveal that hues (grayscale in FIG. 9) abruptly change near the middle of (a) in FIG. 9 along the azimuth direction as compared with (b) in FIG. 9. For this reason, it is estimated that the propagation velocity of a shear wave is low near the middle of (a) in FIG. 9, i.e., the tissue in the target region is softer than that the tissue around the target region in (a) in FIG. 9.

Hues (grayscale in FIG. 9) change moderately near the middle of (b) in FIG. 9 along the azimuth direction as compared with (a) in FIG. 9. For this reason, it is estimated that the propagation velocity of a shear wave is high near the middle of (b) in FIG. 9, i.e., the tissue in the target region is harder than that around the target region in (b) in FIG. 9.

(Modification)

A difference from the first embodiment is that the apparatus decides a corrected arrival time by correcting the shear wave arrival time at each position in a predetermined region with reference to the shear wave arrival time at the designated position designated in the predetermined region in accordance with an instruction from the operator, and generates a corrected shear wave arrival time image by correcting the hues of a shear wave arrival time image, based on the corrected arrival times and an arrival time hue correspondence table. This modification is configured to additionally execute processing for the shear wave arrival time image generated by the first embodiment.

The input unit 9 inputs the designated position designated by the operator to the apparatus main body 5.

The arrival time decision unit 21 decides a corrected arrival time by correcting the shear wave arrival time at each position in a predetermined region with reference to the shear wave arrival time at a designated position. More specifically, the arrival time decision unit 21 decides a corrected arrival time at each position by subtracting the shear wave arrival time at the designated position from the shear wave arrival time at each position. The arrival time decision unit 21 outputs the decided corrected arrival time to the image generation unit 23.

The image generation unit 23 generates a corrected shear wave arrival time image by correcting the hues of the shear wave arrival time image, based on the corrected arrival times and an arrival time hue correspondence table. More specifically, the image generation unit 23 decides hues corresponding to the value of the corrected arrival time at each position by using the arrival time hue correspondence table. The image generation unit 23 generates a corrected shear wave arrival time image by changing the hue of the shear wave arrival time image at each position to a hue corresponding to the corrected arrival time.

The image combining unit 25 generates a corrected superimposed image with corrected hues of a superimposed image by updating the shear wave arrival time image superimposed on a B-mode image to a corrected shear wave arrival time image.

The display unit 7 displays the corrected shear wave arrival time image in place of the displayed shear wave arrival time image. Note that when the display unit 7 is displaying a superimposed image, the display unit 7 may display a corrected superimposed image in place of the displayed superimposed image.

(Corrected Shear Wave Arrival Time Image Generation Function)

The corrected shear wave arrival time image generation function is a function of deciding a corrected arrival time by correcting the shear wave arrival time at each position in a predetermined region with reference to the shear wave arrival time at a designated position and then generating a corrected shear wave arrival time image by correcting the hues of the shear wave arrival time image based on the corrected arrival times and an arrival time hue correspondence table. Processing (to be referred to as corrected shear wave arrival time image generation processing hereinafter) concerning the corrected shear wave arrival time image generation function will be described below.

FIG. 10 is a flowchart showing an example of a procedure for corrected shear wave arrival time image generation processing.

The apparatus inputs a designated position (or a designated region) in a region of interest on the shear wave arrival time image displayed on the display unit 7 in accordance with an instruction from the operator (step Sc1). Note that the designated position may be either a point or a line segment. A line segment as a designated position is, for example, a line segment which passes through the position designated in the region of interest in accordance with an instruction from the operator and is parallel to a scanning line. The apparatus decides a corrected arrival time by correcting the shear wave arrival time at each position with reference to the shear wave arrival time at the designated position (step Sc2). The apparatus reads out an arrival time hue correspondence table from the storage unit 27. The apparatus generates a corrected shear wave arrival time image by correcting the hues of the shear wave arrival time image, based on the readout arrival time hue correspondence table and the corrected arrival times (step Sc3).

FIG. 11 is a view showing a corrected shear wave arrival time image together with a shear wave arrival time image. In FIG. 11, (a) indicates the shear wave arrival time image generated in the first embodiment. In FIG. 11, (b) indicates a corrected shear wave arrival time image generated in this modification. Referring to FIG. 11, shear waves propagate from left to right when facing the drawing surface. Referring to FIG. 11, a circular region 91 indicates a region in which the shear wave velocity is higher than that in a peripheral tissue. Referring to FIG. 11, a circular region 92 indicates a region in which the shear wave velocity is lower than that in the peripheral tissue.

Referring to (a) in FIG. 11, when displaying a corrected shear wave arrival time image, with attention being focused on, for example, the circular region 92, the apparatus inputs a line segment 90 (i.e., a position at which the shear wave arrival time is 0) as a shear wave arrival time reference via the input unit 9. The arrival time decision unit 21 subtracts the shear wave arrival time at a position at the same depth on the line segment 90 (to be referred to as a reference line segment hereinafter) from the shear wave arrival time at a position at the same depth in an ROI. The arrival time decision unit 21 decides a corrected arrival time by executing the above subtraction at each depth in the ROI. If the arrival time is negative, the arrival time decision unit 21 sets the corrected arrival time to 0. The image generation unit 23 generates a corrected shear wave arrival time image by correcting the hues of the shear wave arrival time image, based on the corrected arrival times and the arrival time hue correspondence table.

In FIG. 11, (b) indicates an example of the corrected shear wave arrival time image obtained by correcting the hues of the shear wave arrival time image indicated by (a) in FIG. 11 based on the shear wave arrival times on the reference line segment. As indicated by (b) in FIG. 11, in the region 92, hues (grayscale in FIG. 11) in the azimuth direction abruptly change. That is, (b) in FIG. 11 indicates that the propagation velocity of a shear wave in the region 92 is lower than that in a region around the region 92.

According to the above arrangement, the following effects can be obtained.

The ultrasonic diagnostic apparatus 1 according to this embodiment can generate a shear wave arrival time image with hues being assigned in accordance with shear wave arrival times at the respective positions in a predetermined region, based on a temporal change in the displacement amount of a tissue from which the displacement amount of the tissue due to the body movement of an object is removed. This can visualize, as one image, the manner of the propagation (e.g., refraction and reflection) of shear waves generated in an object. The operator can use this image as information for determining that a region with a patchy pattern in the shear wave arrival time image as a region in which the shear wave arrival times could not be accurately decided because of, for example, a failure of accurately removing displacement amounts due to the body movement of the object. In addition, the operator can exclude a region with a patchy pattern on a shear wave arrival time image from a processing target for the decision of the propagation velocity of a shear wave and an evaluation target for the evaluation of the hardness of a tissue.

In addition, the ultrasonic diagnostic apparatus 1 according to this embodiment can generate a shear wave arrival time image with hues being assigned in accordance with shear wave arrival times at the respective positions in a region of interest by extracting a value having the maximum displacement amount from the maximal values (peaks) of the displacement amount of a tissue from which the displacement amounts of the tissue due to the body movement of the object are removed. These processes of cancelling the body movement and of deciding the arrival time at the respective positions based on the peak of the displacement amount make it possible to robustly decide a proper arrival time even when at least one of the ultrasonic probe and the object moves in displacement amount observation scanning processing.

As described above, according to this embodiment, the operator can grasp the manner of the propagation of shear waves from one shear wave arrival time image without observing an image visualizing the displacement amount at each time as a moving image. The operator can also qualitatively grasp the propagation velocity of a shear wave at each position in a predetermined region, i.e., the hardness of the tissue at each position, by observing the degree of change in hue in the azimuth direction (the manner of change in hue) in a shear wave arrival time image.

According to the modification of this embodiment, the apparatus can generate a corrected shear wave arrival time image with corrected hues corresponding to shear wave arrival times with reference to the shear wave arrival time at the designated position input by the operator via the input unit 9. This makes it possible to easily display the state of a shear wave propagating in a target region to which the operator pays attention even when the target region is spaced apart from the shear wave generation position. In addition, according to the modification of this embodiment, it is possible to designate the position of a shear wave arrival time reference as a line segment. This can initialize the disturbance of a wave front in a target region, even if the wave front of the shear wave is disturbed due to the unevenness of the propagation velocity of the shear wave or the refraction of the shear wave, before the shear wave arrives at the target region. This makes it possible to display the manner of the propagation of a shear wave in a target region so as to make the operator intuitively and easily grasp the manner of the propagation.

Second Embodiment

A difference from the first embodiment is that the apparatus calculates the propagation velocity of a shear wave at each position in a predetermined region (region of interest) by using the shear wave arrival time at each position in the predetermined region, and then generates a shear wave propagation velocity image with hues being assigned in accordance with the calculated propagation velocities.

FIG. 12 is a block diagram showing an example of the arrangement of an ultrasonic diagnostic apparatus according to the second embodiment.

A velocity calculation unit 22 calculates the propagation velocity of a shear wave at each position in a predetermined region by using the shear wave arrival time (arrival time data) at each position in the predetermined region. More specifically, the velocity calculation unit 22 calculates the difference in shear wave arrival time (to be referred to as the arrival time difference hereinafter) between adjacent positions at each position in a predetermined region. In addition, the velocity calculation unit 22 simultaneously calculates the distance between adjacent positions. The velocity calculation unit 22 then calculates, as a shear wave propagation velocity, the product of the reciprocal of the arrival time difference at each position in the predetermined region and the distance between the adjacent positions. The velocity calculation unit 22 outputs the data of the shear wave propagation velocity (to be referred to as the propagation velocity data hereinafter) at each position in the predetermined region to an image generation unit 23.

The image generation unit 23 generates a shear wave propagation velocity image with hues being assigned in accordance with the propagation velocities of shear waves at the respective positions in the predetermined region, based on the propagation velocity data and the propagation velocity hue correspondence table stored in a storage unit 27. The propagation velocity hue correspondence table is the correspondence table of hues corresponding to propagation velocity values. For example, a hue corresponding to a propagation velocity of 0 is blue. For example, hues are sequentially defined as blue, blue-green, green, yellow-green, yellow, orange, and red in ascending order of propagation velocity, with the maximum propagation velocity corresponding to red.

An image combining unit 25 generates a propagation velocity superimposed image by superimposing a shear wave propagation velocity image on a B-mode image upon alignment. The image combining unit 25 outputs the propagation velocity superimposed image or shear wave propagation velocity image to the display unit 7.

The storage unit 27 stores propagation velocity data, a propagation velocity hue correspondence table, shear wave propagation velocity images, propagation velocity superimposed images, an algorithm concerning the generation of shear wave propagation velocity images (to be referred to as a shear wave propagation velocity image generation algorithm hereinafter), and the like.

A CPU 31 reads out a transmission delay pattern, reception delay pattern, shear wave generation transmission delay pattern, and apparatus control program stored in the storage unit 27, based on the selection of a shear wave propagation velocity image display mode input from the operator via an input unit 9, and controls the apparatus main body 5 in accordance with them. For example, the CPU 31 reads out the shear wave propagation velocity image generation algorithm from the storage unit 27. The CPU 31 controls the velocity calculation unit 22, the image generation unit 23, and the like in accordance with the readout shear wave propagation velocity image generation algorithm. The shear wave propagation velocity image display mode is the mode of generating and displaying a shear wave propagation velocity image.

More specifically, upon receiving the shear wave propagation velocity image mode via the input unit 9, the CPU 31 controls the velocity calculation unit 22 to generate propagation velocity data, based on arrival time data. The CPU 31 controls the image generation unit 23 to generate a shear wave propagation velocity image, based on the propagation velocity data and the propagation velocity hue correspondence table read out from the storage unit 27.

The display unit 7 displays a shear wave propagation velocity image, propagation velocity superimposed image, and the like based on outputs from the image combining unit 25.

(Shear Wave Propagation Velocity Image Generation Function)

The shear wave propagation velocity image generation function is a function of generating a shear wave propagation velocity image which represents the propagation velocity of a shear wave at each position in a predetermined region (second region) by a hue. Processing (to be referred to as shear wave propagation velocity image generation processing hereinafter) concerning the shear wave propagation velocity image generation function will be described below.

FIG. 13 is a flowchart showing an example of a procedure for shear wave propagation velocity image generation processing.

The apparatus calculates the propagation velocity of a shear wave at each position in a predetermined region based on the shear wave arrival time at each position (step Sd1). The apparatus generates a shear wave propagation velocity image with hues being assigned in accordance with the propagation velocities of shear waves at the respective positions in the predetermined region, based on the propagation velocities at the respective positions and the propagation velocity hue correspondence table (step Sd2).

(First Modification)

A difference from the second embodiment is that the apparatus calculates the average propagation velocity of a shear wave in a designated region (to be referred to as the intra-region average propagation velocity hereinafter) designated in a predetermined region in accordance with an instruction from the operator, and displays the intra-region average propagation velocity.

The input unit 9 inputs the designated region designated in a predetermined region by the operator to the apparatus main body 5.

The velocity calculation unit 22 calculates an intra-region average propagation velocity based on the shear wave arrival time at each position in the designated region and the distance from the shear wave generation position to each position in the designated region. For example, the velocity calculation unit 22 calculates an intra-region average propagation velocity by linear regression analysis based on a plurality of shear wave arrival times at positions on different scanning lines at the same depth in the designated region and the distance from the shear wave generation position to each position.

The image generation unit 23 generates an image displaying the intra-region average propagation velocity together with the shear wave arrival time image.

FIG. 14 is a graph obtained by plotting shear wave propagation data at the respective positions at the same depth on four different scanning lines in a designated region, with the ordinate representing the displacement amount and the abscissa representing the time. Curves 64, 65, 66, and 67 in FIG. 14 represent shear wave propagation data at the same depth on respectively different scanning lines. The curves 64, 65, 66, and 67 in FIG. 14 respectively correspond to scanning lines 54, 55, 56, and 57 in FIG. 3. The arrival time decision unit 21 decides, as a shear wave arrival time, the time corresponding to the maximum value in a direction away from the ultrasonic probe (negative displacement amounts in FIG. 14) with respect to each of the curves 64, 65, 66, and 67 in FIG. 14.

FIG. 15 is a graph showing an example of the relationship between shear wave arrival time and distance from the shear wave generation position. A point 74 in FIG. 15 indicates the distance from the shear wave generation position corresponding to the shear wave arrival time decided with respect to the curve 64 in FIG. 14. A point 75 in FIG. 15 indicates the distance from the shear wave generation position corresponding to the shear wave arrival time decided with respect to the curve 65 in FIG. 14. A point 76 in FIG. 15 indicates the distance from the shear wave generation position corresponding to the shear wave arrival time decided with respect to the curve 66 in FIG. 14. A point 77 in FIG. 15 indicates the distance from the shear wave generation position corresponding to the shear wave arrival time decided with respect to the curve 67 in FIG. 14. A straight line 78 in FIG. 15 is an approximate straight line decided by linear regression analysis using the points 74, 75, 76, and 77. The velocity calculation unit 21 calculates the slope of a straight line by linear regression analysis as an intra-region average propagation velocity.

(Second Modification)

A difference from the first modification of the second embodiment is that the apparatus calculates an average elastic modulus in a designated region by using a calculated intra-region average propagation velocity.

The velocity calculation unit 22 calculates an average elastic modulus (Young's modulus) by using the calculated intra-region average propagation velocity. More specifically, the velocity calculation unit 22 calculates an average elastic modulus (E(kPa)) by multiplying the square ($v_s^2$) of the intra-region average propagation velocity ($v_s$ (m/s)) by 3 ($3 \times v_s^2$). That is, the velocity calculation unit 22 calculates $E = 3 \times v_s^2$.

The image generation unit 23 generates an image for calculating an average elastic modulus, together with a shear wave arrival time image.

A display unit 7 displays an image for calculating an average elastic modulus, together with a shear wave arrival time image.

With the above arrangement, the following effects can be obtained.

The ultrasonic diagnostic apparatus 1 according to this embodiment calculates the propagation velocity of a shear wave at each position in a predetermined region (region of interest) by using the shear wave arrival time at each position in the predetermined region, and generates a shear wave propagation velocity image with hues being assigned in accordance with the calculated propagation velocities. This makes it possible to visualize the spatial distribution of the propagation velocities of shear waves generated in an object. In addition, the operator can determine that the propagation of shear waves has not been properly captured in a region in which the propagation velocities of the shear waves are uneven in terms of noise. The apparatus can further show shear wave arrival time image and allow users to designate a region in which shear waves have propagated or a region in which the propagation of shear waves has been accurately captured on that shear wave arrival time image as a region for analyzing the average propagation velocity of shear waves and an average elastic modulus, and calculate the average propagation velocity of shear waves and an average elastic modulus. This makes it possible to improve the reliability of quantitative analysis results such as the average propagation velocity of shear waves and an average elastic modulus.

In addition, when the technical idea of the ultrasonic diagnostic apparatus 1 is to be implemented by a medical image processing apparatus 100 as a modification of the first embodiment, for example, the apparatus includes the constituent elements in the dotted line in the block diagram of FIG. 1. Note that the medical image processing apparatus 100 can store the first and second displacement data in the storage unit 27 and execute the following processing. In this case, the apparatus does not require the displacement amount calculation unit 19. The medical image processing apparatus 100 can also store shear wave propagation data in the storage unit 27 and execute the following processing. In this case, the apparatus does not require the displacement amount calculation unit 19 and the arrival time decision unit 21.

Furthermore, when the technical idea of the ultrasonic diagnostic apparatus 1 is to be implemented by a medical image processing apparatus 101 as a modification of the second embodiment, for example, the apparatus includes the constituent elements in the dotted line in the block diagram of FIG. 12. The medical image processing apparatus 101 can also load the shear wave arrival time image data and the like output from the ultrasonic diagnostic apparatus 1 and execute the above processing.

Third Embodiment

A difference from the first and second embodiments is that the apparatus executes the transmission of a push pulse in accordance with each of a plurality of observation scanning lines a plurality of times. A case in which the apparatus transmits a plurality of push pulses to a plurality of focal points at different depths in the first region will be described as a specific example.

A transmission unit 11 transmits a plurality of push pulses respectively corresponding to a plurality of focal points at different depths in the first region. Transmitting a plurality of push pulses will generate shear waves at the respective focal points. A superimposed shear wave obtained by superimposing the shear waves generated at the plurality of focal points propagates in the second region. The transmission unit 11 respectively transmits, for example, push pulses to four focal points at different depths in the first region. More specifically, in step Sa3 in FIG. 2, the transmission unit 11 transmits push pulses to four focal points, respectively.

The second displacement data obtained by the autocorrelation computation device or cross-correlation computation device of a Doppler processing unit 17 has the displacement amount of a tissue originating from a superimposed shear wave.

A displacement amount calculation unit 19 calculates superimposed shear wave propagation data representing a temporal change in the tissue displacement amount caused by the superimposed shear wave by subtracting body movement displacement data from the first and second displacement data.

An arrival time decision unit 21 decides a shear wave arrival time based on a temporal change in the displacement amount of the tissue in the superimposed shear wave propagation data. More specifically, the arrival time decision unit 21 decides, as a shear wave arrival time, the time corresponding to the maximum value of the displacement amount of a tissue in superimposed shear wave propagation data at each position in a predetermined region, with the transmission start or end time of one of push pulses being 0. The arrival time decision unit 21 outputs the arrival time data at each position in the predetermined region to an image generation unit 23. Note that it is possible to arbitrarily select the transmission start time or transmission end time of one of push pulses as a reference time for a shear wave arrival time.

According to the above arrangement, the following effects can be obtained.

An ultrasonic diagnostic apparatus 1 according to this embodiment can generate a shear wave arrival time image with hues being assigned in accordance with superimposed shear wave arrival times at the respective positions in a region of interest, based on a temporal change in the displacement amount of a tissue from which the displacement amount of the tissue due to the body movement of an object is removed. This can visualize the manner of the propagation (e.g., refraction and reflection) of shear waves generated in an object as one image.

An ultrasonic diagnostic apparatus connected to medical image processing apparatuses 100 and 101 via a network may execute acquisition and storage of data in an ultrasonic examination. It is possible to use the medical image processing apparatuses 100 and 101 to closely observe shear wave arrival time images after an ultrasonic examination. That is, this embodiment exhibits its effect when an examiner who performs an ultrasonic examination differs from an analyzer who analyzes the medical images generated by the ultrasonic diagnostic apparatus. That is, the analyzer can check from a shear wave arrival time image, after an ultrasonic examination, whether shear waves have propagated in a manner desired by the analyzer. The analyzer can calculate the elastic modulus of a tissue in a predetermined region based on the shear wave arrival time image. This can improve, for example, the reliability of the elastic modulus as an analysis result. In addition, it is possible to prevent the analyzer from subjectively deciding an analysis range. This can reduce the possibility of misdiagnosis.

In addition, each function according to the embodiments can be implemented by installing programs for executing the processing in a computer such as a workstation and expanding them in the memory. In this case, the programs which can cause the computer to execute the corresponding techniques can be distributed by being stored in storage media such as magnetic disks (hard disks and the like), optical disks (CD-ROMs, DVDs, and the like), and semiconductor memories.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
   an ultrasonic probe configured to perform an ultrasound transmission for generating a shear wave, and perform ultrasound scans for a region where the shear wave propagates; and
   processing circuitry configured to:
      calculate displacement amounts of each position in the region over time based on reception signals generated by the ultrasound scans;
      determine an arrival time when the shear wave has arrived, for each position in the region, based on a temporal change in the displacement amounts of the position, the arrival time of the position being relative to a reference time that indicates when the shear wave propagating in the region has arrived at a point corresponding to the position and located along a reference line that is designated within the region, the reference time varying depending on when the shear wave arrives at points located along the reference line; and
      generate and control a display to display a shear wave arrival time image formed by pixels, a pixel value at each of the pixels representing the arrival time at each of positions in the region and being assigned a hue corresponding to the arrival time.

2. The ultrasonic diagnostic apparatus of claim 1, wherein the processing circuitry is further configured to determine the arrival time based on a maximum displacement amount of the displacement amounts.

3. The ultrasonic diagnostic apparatus of claim 1, wherein the processing circuitry is further configured to determine the arrival time based on a maximum displacement amount of maximal values of temporal changes in the displacement amount.

4. The ultrasonic diagnostic apparatus of claim 1, wherein the processing circuitry is further configured to determine the arrival time based on a maximum time change of temporal changes in the displacement amount.

5. The ultrasonic diagnostic apparatus of claim 1, wherein the processing circuitry is further configured to calculate the displacement amounts along a direction away from the ultrasonic probe as the displacement amount.

6. The ultrasonic diagnostic apparatus of claim 1, further comprising
a peripheral device configured to input a designated region designated by an operator, wherein the processing circuitry is configured to
determine a corrected arrival time at the each position with reference to the reference time for the designated region, and
generate a corrected shear wave arrival time image by correcting a pixel value in the shear wave arrival time image, based on the corrected arrival time and the pixel value.

7. The ultrasonic diagnostic apparatus of claim 1, wherein the processing circuitry is further configured to:
calculate a propagation velocity of a shear wave at the each position by using the arrival time at the each position; and
generate, based on the calculated propagation velocities and pixel values set in advance in accordance with the propagation velocities, a shear wave propagation velocity image with the pixel values being assigned in accordance with the propagation velocities at the respective positions.

8. The ultrasonic diagnostic apparatus of claim 1, further comprising:
a peripheral device configured to input a designated region designated by an operator,
wherein the processing circuitry is further configured to calculate a propagation velocity of a shear wave propagating in the designated region by using the arrival time at each position in the designated region.

9. The ultrasonic diagnostic apparatus of claim 1, further comprising:
a peripheral device configured to input a designated region designated by an operator,
wherein the processing circuitry is further configured to calculate an elastic modulus in the designated region by using a propagation velocity of the shear wave propagating in the designated region.

10. A medical image processing apparatus comprising:
a storage configured to store a reception signal; and
processing circuitry configured to:
calculate tissue displacement amounts of each position in a region over time based on reception signals generated by an ultrasound scans;
determine an arrival time when a shear wave has arrived, for each position in the region, based on a temporal change in the tissue displacement amounts of the position, the arrival time of the position being relative to a reference time that indicates when the shear wave propagating in the region has arrived at a point corresponding to the position and located along a reference line that is designated within the region, the reference time varying depending on when the shear wave arrives at points located along the reference line; and
generate and control a display to display a shear wave arrival time image formed by pixels, a pixel value at each of the pixels representing the arrival time at each of positions in the region.

11. A medical image processing method comprising:
storing a reception signal;
calculating tissue displacement amounts of each position in a region over time based on reception signals generated by an ultrasound scans;
determining an arrival time when a shear wave has arrived, for each position, based on a temporal change in the tissue displacement amounts of the position, the arrival time of the position being relative to a reference time that indicates when the shear wave propagating in the region has arrived at a point corresponding to the position and located along a reference line that is designated within the region, the reference time varying depending on when the shear wave arrives at points located along the reference line; and
generating and controlling a display to display a shear wave arrival time image formed by pixels, a pixel value at each of the pixels representing the arrival time at each of positions in the region and being assigned a hue corresponding to the arrival time.

12. An ultrasonic diagnostic apparatus comprising:
an ultrasonic probe configured to perform an ultrasound transmission for generating a shear wave, and perform ultrasound scans for a region where the shear wave propagates; and
processing circuitry configured to:
calculate displacement amounts of each position of the region over time based on reception signals generated by the ultrasound scans;
obtain a body movement displacement amount which is a displacement amount based on a body movement of an object to be scanned, and subtract the body movement displacement amount from the displacement amounts;
determine an arrival time when the shear wave has arrived, for each position in the region, based on a temporal change in the subtraction result displacement amounts of the position, the arrival time of the position being relative to a reference time that indicates when the shear wave propagating in the region has arrived at a point corresponding to the position and located along a reference line that is designated within the region, the reference time varying depending on when the shear wave arrives at points located along the reference line; and
generate and control a display to display a shear wave arrival time image formed by pixels, a pixel value at each of the pixels representing the arrival time at each of positions in the region and being assigned a hue corresponding to the arrival time.

\* \* \* \* \*